US006969724B2

(12) United States Patent
Barlocco et al.

(10) Patent No.: US 6,969,724 B2
(45) Date of Patent: Nov. 29, 2005

(54) COMPOUNDS

(75) Inventors: Daniela Barlocco, Milan (IT); Giorgio Cignarella, Milan (IT); Giuseppe Arnaldo Maria Giardina, Milan (IT); Mario Grugni, Milan (IT); Silvano Ronzoni, Milan (IT)

(73) Assignee: SmithKline Beecham-SpA, Brentford (GB)

( * ) Notice: Subject to any disclaimer, the term of this patent is extended or adjusted under 35 U.S.C. 154(b) by 0 days.

(21) Appl. No.: 10/324,571

(22) Filed: Dec. 19, 2002

(65) Prior Publication Data

US 2004/0024218 A1 Feb. 5, 2004

Related U.S. Application Data

(63) Continuation of application No. 09/831,469, filed as application No. PCT/EP99/08706 on Nov. 10, 1999, now abandoned.

(30) Foreign Application Priority Data

Nov. 11, 1998 (IT) .......................... MI98A2442

(51) Int. Cl.$^7$ ..................... A61K 31/445; C07D 211/14
(52) U.S. Cl. ....................... 514/319; 546/206; 546/205; 546/203
(58) Field of Search ................. 514/319, 326, 514/330; 546/206, 205, 203, 226, 236

(56) References Cited

U.S. PATENT DOCUMENTS

| | | | | |
|---|---|---|---|---|
| 3,812,119 A | * | 5/1974 | Walker | 514/319 |
| 4,022,791 A | * | 5/1977 | Welch, Jr. | 514/319 |
| 5,489,599 A | * | 2/1996 | Carter et al. | 514/317 |

FOREIGN PATENT DOCUMENTS

| | | |
|---|---|---|
| DE | 28 343 72 A | 2/1979 |
| DE | 36 20 358 A | 12/1986 |
| EP | 0 825 180 A | 2/1998 |
| GB | 2 091 250 | 7/1982 |
| GB | 2 177 085 A | 1/1987 |
| WO | WO 98 02432 A | 1/1998 |
| WO | WO 98 36749 A | 8/1998 |
| WO | WO 00/06545 | 2/2000 |

OTHER PUBLICATIONS

Welch, Willard, et al., "Analgesic and Tranquilizing Activity of 5,8–Disubstituted 1–Tetralone Mannich Bases" JOURNAL OF MEDICINAL CHEMISTRY, 1977, vol. 20, No. 5 pp. 699–705, XP–000882092.

Santana, L., et al., "Sintesis de 2–aminometiltetralines como agentes α–bioqueantes y antidopamincergicos", ANALES DE LA REAL ACADEMIE DE FARMACIA, Vol. 55, Apr. 1989, pp. 461–469, XP–000882145.

Neunier, Jean–Claude, "Nociceptin/orphanin FQ and the opioid receptor–like ORL1 receptor",EUROPEAN JOURNAL OF PHARMACOLOGY, NL, ELSEVIER SCIENCE B.V. AMSTERDAM, Vol. 340, Jan. 1997 pp. 1–15, XP 000872550.

Henderson, Graeme & McKnight, Alexander T., The Orphan Opioid receptor and its endogenous ligand–nociceptin/orphanian FQ, TRENDS IN PHARMOACOLOGICAL SCIENCES, G. ELSEVIER SCIENCE LTD., Vol. 18, No. 8, Aug. 1, 1997, pp. 293–300, XP004085920.

Zaki, Paulette A. & Evans, Chris J., "ORL–1: An Awkward Child of the Opioid Receptor Family", THE NEUROSCIENTIST, Vol. 4, No. 3, Mar. 1998, pp. 172–184, XP 000872580.

* cited by examiner

Primary Examiner—Charanjit S. Aulakh
(74) Attorney, Agent, or Firm—Andrea L. Winslow; Nora Stein; Charles M. Kinzig

(57) ABSTRACT

Compounds of formula I, or a salt thereof or a hydrate thereof, as follows:

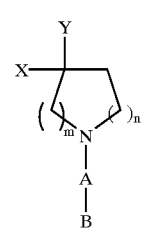

wherein

X and Y are selected independently from hydrogen and aryl, which aryl is unsubstituted or substituted one or more times by hydroxy, hydroxyC$_{1-6}$alkyl, C$_{1-6}$alkoxyC$_{1-6}$alkyl, aryl, heterocyclyl, amino, C$_{1-6}$alkylamino, di(C$_{1-6}$alkyl)amino, arylC$_{1-6}$alkoxy, C$_{1-6}$alkyl, C$_{1-6}$alkoxy or halo, which alkyl or alkoxy groups are unsubstituted or substituted one or more times by halo;

m and n are independently 0 to 3, provided that m and n are not both 0;

A represents a single bond or is —(CR$_{pa}$ R$_{pb}$)$_p$— wherein p is 1–3 and R$_{pa}$ and R$_{pb}$ are selected independently from hydrogen, C$_{1-6}$alkyl, C$_{1-6}$alkoxy and halo, which alkyl or alkoxy groups are independently substituted one or more times by halo;

B represents a C$_{4-8}$ saturated or unsaturated ring, which ring is unsubstituted or substituted one or more times by C$_{1-6}$alkyl, C$_{1-6}$alkoxy, aryl, aryloxy, hydroxy, oxo, halo, amino, C$_{1-6}$alkylamino, di(C$_{1-6}$ alkyl)amino, and C$_{1-6}$alkylamido, which C$_{1-6}$alkyl or C$_{1-6}$alkoxy groups are unsubstituted or substituted one or more times by halo, which aryl group is unsubstituted or substituted one or more times by aryl, heterocyclyl, aryloxy, arylC$_{1-6}$alkoxy, amino, C$_{1-6}$alkylamino, di(C$_{1-6}$alkyl)amino, arylC$_{1-6}$alkyl, hydroxy, C$_{1-6}$alkenoxy, C$_{1-6}$alkoxy, halo, or C$_{1-6}$alkyl, which C$_{1-6}$alkyl may be substituted one or more times by halo, and which aryl group is linked to said ring by a single bond or is benzo-condensed therewith are ligands of the ORL-1 receptor.

6 Claims, No Drawings

COMPOUNDS

This is a continuation of application Ser. No. 09/831,469 filed May 9, 2001 now abandoned, which claims priority to PCT/EP99/08706 filed Nov. 10, 1999.

The present invention relates to certain novel compounds, to processes for preparing such compounds, to pharmaceutical compositions containing such compounds, and to the use of such compounds in medicine.

The ORL-1 receptor is found throughout the whole of the neuraxis and is known to be involved in the transmission of pain.

European Patent Application EP-A-0856514 (F. Hofmann-LaRoche A G) discloses 8-substituted-1,3,8-triaza-spiro[4.5]decan-4-one derivatives that are agonists and/or antagonists of the ORL-1 receptor. Said ORL-1 receptor is also known as the nociceptin/OFQ receptor.

Eur. J. Med. Chem. 1978; 13:533–547 (Eirin et al.) discloses (±)-3-[(4-phenylpiperidin-1-yl)methyl]-1-oxo-2H-3,4-dihydronaphthalene for use as a neuroleptic agent.

An. Real. Acad. Farm. 1989; 55:461–469 (Santana et al.) discloses (±)-2-[(4-phenylpiperidin-1-yl)methyl]-1,2,3,4-tetrahydronaphthalene as an antidopaminergic agent.

U.S. Pat. No. 3,812,119 (Ciba-Geigy Corporation) discloses certain dibenzocycloheptenes that have utility as antidepressants.

U.S. Pat. No. 4,022,791 (Pfizer Inc.) discloses certain 2-aminomethyl-3,4-dihydronaphthalenes as analgesics.

J. Med. Chem. 1977; 20(5):699–705 (Welch et al) discloses 5,8-disubstituted 1-tetralones as analgesics and tranquillisers.

J. Med. Chem. 1978; 21(3):257–263 (Welch et al) discloses certain 5,8-disubstituted 2-aminomethyl-3,4-dihydronaphthalenes as analgesics and tranquillisers.

International Application Publication Number WO 98/36749 (Bristol-Myers Squibb) discloses certain tetralone derivatives as antiarrhythmic agents.

United Kingdom Patent Application GB2177084 (Imperial Chemical Industries PLC) discloses certain benzopyran derivatives as fungicides.

United Kingdom Patent Application GB2177085 (Imperial Chemical Industries PLC) discloses certain benzocycloalkylmethylamines as fungicides.

Co-pending International Application Publication Number WO 99/06397 (Abbott Laboratories) discloses certain piperidine compounds useful as endothelin antagonists.

International Application Publication Number WO 98/02432 (Takeda Chemical Industries Ltd) discloses certain phenylpiperidino compounds useful for the treatment of lower urinary tract infections.

International Application Publication Number WO 96/22977 discloses certain piperidinyl derivatives for treating symptoms of ischaemic diseases and preventing cytotoxic calcium overload.

International Application Publication Number WO 97/23458 (Cocensys Inc.) discloses certain tetrahydronaphthyl and piperidine derivatives as sub-type selective N-methyl-D-aspartame receptor ligands.

U.S. Pat. No. 5,436,255 (Pfizer Inc.) discloses certain 3-piperidino-1-chromanol derivatives for blocking the NMDA receptor site.

International Application Publication Number WO 95/00131 (University of Virginia Commonwealth) discloses certain amine derivatives as useful in the treatment of CNS disorders.

European Patent Application EP 0 745 598 (Adir et Compagnie) discloses certain piperazine, piperidine, and tetrahydropyridine compounds as ligands of the $D_4$ dopamine receptor.

European Patent Application EP 0 742 207 (Eisai Co. Ltd.) discloses certain cyclic amines as having acetylcholine esterase activity.

U.S. Pat. No. 5,215,989 (Merck & Co. Inc.) discloses certain disubstituted piperazine and imidazole derivatives useful as Class III antiarrhythmic agents.

International Application Publication Number WO 93/00313 (University of Virginia Commonwealth) discloses certain amine derivatives as selective sigma receptor binding agents.

European Patent Application EP 0 479 601 (Ajinomoto K K) discloses certain piperidine derivatives as antiarrhythmic agents.

Japanese Patent Application JP 2169 569 (Eisai K K) discloses certain cyclic amine derivatives for the treatment or prophylaxis of e.g. senile dementia, cerebral apoplexy, and cerebral atherosclerosis.

It has now been found that certain nitrogen heterocycles are ligands of the ORL-1 receptor, and therefore may be useful as an analgesic in humans or animals for the treatment, for example, of acute pain; chronic neuropathic or inflammatory pain, including post herpetic neuralgia, neuralgia, diabetic neuropathy and post stroke pain; osteoarthritis/back pain; and painful pregnancy labour.

These compounds may also therefore be useful in the treatment or prophylaxis of eating disorders, such as anorexia and bulimia; anxiety and stress conditions; immune system diseases; cardiovascular system dysfunctions; memory loss, cognitive disorders, motor impairment and neurodegeneration owing to Alzheimer's disease, senile dementia, Parkinson's disease or other neurodegenerative pathologies; stroke; epilepsy; altered diuresis and sodium excretion; syndrome of inappropriate secretion of antidiuretic hormone (SIADH); adult respiratory distress syndrome (ARDS); congestive heart failure; cirrhosis with ascites; sexual dysfunctions including impotence and frigidity; and altered pulmonary function, including chronic obstructive pulmonary disease.

Accordingly, the present invention provides a compound of formula I

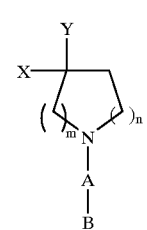

or a salt thereof or a hydrate thereof
wherein

X and Y are selected independently from hydrogen and aryl, which aryl is unsubstituted or substituted one or more times by hydroxy, hydroxy$C_{1-6}$alkyl, $C_{1-6}$alkoxy$C_{1-6}$alkyl, aryl, heterocyclyl, amino, $C_{1-6}$alkylamino, di($C_{1-6}$alkyl)amino, aryl$C_{1-6}$alkoxy, $C_{1-6}$alkyl, $C_{1-6}$alkoxy or halo, which alkyl or alkoxy groups are unsubstituted or substituted one or more times by halo;

m and n are independently 0 to 3, provided that m and n are not both 0;

A represents a single bond or is —$(CR_{pa}R_{pb})_p$— wherein p is 1–3 and $R_{pa}$ and $R_{pb}$ are selected independently from hydrogen, $C_{1-6}$alkyl, $C_{1-6}$alkoxy and halo, which alkyl or alkoxy groups are independently substituted one or more times by halo;

B represents a $C_{4-8}$ saturated or unsaturated ring, which ring is unsubstituted or substituted one or more times by $C_{1-6}$alkyl, $C_{1-6}$alkoxy, $C_{1-6}$alkenoxy, aryl, aryloxy, hydroxy, oxo, halo, amino, $C_{1-6}$alkylamino, di($C_{1-6}$ alkyl) amino, and $C_{1-6}$alkylamido, which $C_{1-6}$alkyl or $C_{1-6}$alkoxy groups are unsubstituted or substituted one or more times by halo, which aryl group is unsubstituted or substituted one or more times by aryl, heterocyclyl, aryloxy, aryl$C_{1-6}$alkoxy, amino, $C_{1-6}$alkylamino, di($C_{1-6}$ alkyl)amino, aryl$C_{1-6}$alkyl, hydroxy, $C_{1-6}$alkenoxy, $C_{1-6}$alkoxy, halo, or $C_{1-6}$alkyl, which $C_{1-6}$alkyl may be substituted one or more times by halo, and which aryl group is linked to said ring by a single bond or is benzo-condensed therewith;

subject to the proviso that the compounds on the list below (hereinafter referred to as List A) are excluded:

10-[(4-phenylpiperidin-1-yl)methyl]-10,11-dihydro-5H-dibenzo[a,d]cycloheptene;

2-[(4-phenylpiperidin-1-yl)methyl]-6-methoxy-2-methyl-1-oxo-2H-3,4-dihydronaphthalene;

2-[(4-phenylpiperidin-1-yl)methyl]-6-methoxy-1-oxo-2H-3,4-dihydronaphthalene;

2-[(4-phenylpiperidin-1-yl)methyl]-5-methoxy-1-oxo-2H-3,4-dihydronaphthalene;

2-[(4-phenylpiperidin-1-yl)methyl]-6-ethyl-1-oxo-2H-3,4-dihydronaphthalene;

2-[(4-phenylpiperidin-1-yl)methyl]-6-benzyloxy-1-oxo-2H-3,4-dihydronaphthalene;

2-[(4-phenylpiperidin-1-yl)methyl]-1-oxo-6-phenylethoxy-2H-3,4-dihydronaphthalene;

2-[(4-phenylpiperidin-1-yl)methyl]-1-oxo-6-phenoxy-2H-3,4-dihydronaphthalene;

2-[(4-phenylpiperidin-1-yl)methyl]-1-oxo-6-phenyl-2H-3,4-dihydronaphthalene;

2-[(4-phenylpiperidin-1-yl)methyl]-5-methoxy-2-methyl-1-oxo-2H-3,4-dihydronaphthalene;

2-[(4-phenylpiperidin-1-yl)methyl]-2-methyl-1-oxo-6-phenoxy-2H-3,4-dihydronaphthalene;

2-[(4-phenylpiperidin-1-yl)methyl]-2-methyl-1-oxo-6-phenyl-2H-3,4-dihydronaphthalene;

2-[(4-phenylpiperidin-1-yl)methyl]-1-hydroxy-6-methoxy-1,2,3,4-tetrahydronaphthalene;

2-[(4-phenylpiperidin-1-yl)methyl]-1-hydroxy-6-methoxy-2-methyl-1,2,3,4-tetrahydronaphthalene;

2-[(4-phenylpiperidin-1-yl)methyl]-1-hydroxy-6-(2-phenyl)benzyloxy-1,2,3,4-tetrahydronaphthalene;

2-[(4-phenylpiperidin-1-yl)methyl]-1-acetamido-6-methoxy-2-methyl-1,2,3,4-tetrahydronaphthalene;

2-[(4-phenylpiperidin-1-yl)methyl]-1-amino-6-methoxy-2-methyl-1,2,3,4-tetrahydronaphthalene;

2-[(4-phenylpiperidin-1-yl)methyl]-1,2,3,4-tetrahydronaphthalene;

2-[(4-phenylpiperidin-1-yl)methyl]-7-fluoro-1,2,3,4-tetrahydronaphthalene;

3-[(4-phenylpiperidin-1-yl)methyl]-1-oxo-2H-3,4-dihydronaphthalene;

3-[(4-phenylpiperidin-1-yl)methyl]-6-fluoro-1-oxo-2H-3,4-dihydronaphthalene;

2-[(4-phenylpiperidin-1-yl)methyl]-6-methoxy-1,2,3,4-tetrahydronaphthalene;

2-[(4-phenylpiperidin-1-yl)methyl]-1-oxo-2H-3,4-dihydronaphthalene;

2-[(4-phenylpiperidin-1-yl)methyl]-8-chloro-5-methoxy-2H-3,4-dihydronaphthalene;

2-[(4-phenylpiperidin-1-yl)methyl]-8-chloro-5-methoxy-1-oxo-2H-3,4-dihydronaphthalene, and;

2-[(4-phenylpiperidin-1-yl)methyl]-5-methoxy-1-oxo-2H-2,3-dihydroindene.

There exists a ether group of compounds of formula IA

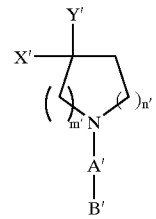

IA wherein

X', Y', A', B', m', and n' are as defined for X, Y, A, B, m, and n respectively in formula I, but which includes the compounds of List A.

Compounds of formula I and formula IA may exhibit stereoisomerism by virtue of the presence of chiral atoms and/or multiple bonds. The present invention therefore extends to the stereoisomers of compounds of formula I, including racemates, enantiomers, diastereoisomers, and geometrical isomers.

It has been found that, where a compound of formula I or formula IA exhibits optical isomerism, one enantiomer possesses a greater affinity for the ORL-1 receptor than its antipode.

Accordingly, the present invention also provides an enantiomer of a compound of formula I.

In a further aspect, the present invention provides a mixture of enantiomers of a compound of formula I wherein one enantiomer is present in a greater proportion than its antipode.

As has previously been mentioned, compounds of formula I are ligands of the ORL-1 receptor. Compounds of formula IA are also ligands of the ORL-1 receptor.

Thus, there is provided a compound of formula I as an active therapeutic substance.

According to another aspect of the present invention there is provided a method of modulating the ORL-1 receptor activity in a human or animal patient in need thereof, which method comprises administering to the human or animal patient an effective amount of a compound of formula IA.

In yet another aspect of the present invention there is provided the use of a compound of formula IA in the manufacture of a medicament for administration to a human or animal patient for modulating the ORL-1 receptor activity.

Said compounds of formula I and formula IA may be agonists or antagonists of the ORL-1 receptor.

In accordance with a particular aspect of the present invention, an antagonist of formula I may be used as an analgesic in humans or animals for the treatment, for example, of acute pain; chronic neuropathic or inflammatory pain, including post herpetic neuralgia, neuralgia, diabetic neuropathy and post stroke pain; osteoarthritis/back pain; and painful pregnancy labour.

In accordance with a further aspect of the invention, compounds of formula I may be used in the treatment or prophylaxis of eating disorders, such as anorexia and bulimia; anxiety and stress conditions; immune system diseases; cardiovascular system dysfunctions; memory loss, cognitive disorders, motor impairment and neurodegeneration owing to Alzheimer's disease, senile dementia, Parkinson's disease or other neurodegenerative pathologies; stroke; epilepsy; altered diuresis and sodium excretion; syndrome of inappropriate secretion of antidiuretic hormone (SIADH); adult respiratory distress syndrome (ARDS); congestive heart failure; cirrhosis with ascites; sexual dysfunctions including impotence and frigidity; and altered pulmonary function, including chronic obstructive pulmonary disease.

In some embodiments, X and Y of formula I above may be selected independently from hydrogen and unsubstituted or substituted phenyl.

Suitably X is unsubstituted phenyl or phenyl substituted with $C_{1-6}$alkyl, $C_{1-6}$alkoxy, hydroxy, halo, or aryl$C_{1-6}$alkoxy.

Favourably, X is unsubstituted phenyl or phenyl substituted with methyl, methoxy, hydroxy, fluoro, benzyloxy, bromo, or chloro.

Preferably, X is unsubstituted phenyl, or phenyl substituted with methyl, fluoro, or chloro.

Most preferably, X is phenyl substituted with methyl.

Preferably, Y is hydrogen.

Suitably, m and n are independently 1 or 2, typically one of m and n is 1 and the other is 2.

Preferably m is 2 and n is 1.

Suitably, A is —$(CR_{pa} R_{pb})_p$— wherein p is 1–3 and $R_{pa}$ and $R_{pb}$ are selected independently from hydrogen, $C_{1-6}$alkyl, $C_{1-6}$alkoxy and halo, which alkyl or alkoxy groups are independently substituted one or more times by halo.

Preferably A is —$CH_2$—.

Suitably, B represents a $C_{4-8}$ saturated or unsaturated ring, which ring is unsubstituted or substituted once by aryl and/or one or more times by $C_{1-6}$alkyl, $C_{1-6}$alkoxy, $C_{1-6}$alkenoxy, aryloxy, hydroxy, oxo, halo, amino, $C_{1-6}$alkylamino, di($C_{1-6}$alkyl)amino, and $C_{1-6}$alkylamido, which $C_{1-6}$alkyl or $C_{1-6}$alkoxy groups are unsubstituted or substituted one or more times by halo, which aryl group is unsubstituted or substituted one or more times by aryl, heterocyclyl, aryloxy, aryl$C_{1-6}$alkoxy, amino, $C_{1-6}$alkylamino, di($C_{1-6}$alkyl)amino, aryl$C_{1-6}$alkyl, hydroxy, $C_{1-6}$alkenoxy, $C_{1-6}$alkoxy, halo, or $C_{1-6}$alkyl, which $C_{1-6}$alkyl may be substituted one or more times by halo, and wherein the aryl group is linked to said ring by a single bond or is benzo-condensed therewith.

Suitably, B represents a $C_{4-8}$ unsaturated ring, or a $C_4$, $C_7$, or $C_8$ saturated ring, which ring is unsubstituted or substituted one or more times by $C_{1-6}$alkyl, $C_{1-6}$alkoxy, $C_{1-6}$alkenoxy, aryl, aryloxy, hydroxy, oxo, halo, amino, $C_{1-6}$alkylamino, di($C_{1-6}$ alkyl)amino, and $C_{1-6}$alkylamido, which $C_{1-6}$alkyl or $C_{1-6}$alkoxy groups are unsubstituted or substituted one or more times by halo, which aryl group is unsubstituted or substituted one or more times by aryl, heterocyclyl, aryloxy, aryl$C_{1-6}$alkoxy, amino, $C_{1-6}$alkylamino, di($C_{1-6}$alkyl)amino, aryl$C_{1-6}$alkyl, hydroxy, $C_{1-6}$alkenoxy, $C_{1-6}$alkoxy, halo, or $C_{1-6}$alkyl, which $C_{1-6}$alkyl may be substituted one or more times by halo, and wherein the aryl group is linked to said ring by a single bond or is benzo-condensed therewith.

Suitably, B represents a $C_{4-8}$ saturated or unsaturated ring, which ring is substituted one or more times by $C_{1-6}$alkyl, $C_{1-6}$alkoxy, $C_{1-6}$alkenoxy, aryl, aryloxy, hydroxy, halo, amino, $C_{1-6}$alkylamino, di($C_{1-6}$ alkyl)amino, and $C_{1-6}$alkylamido, which $C_{1-6}$alkyl or $C_{1-6}$alkoxy groups are unsubstituted or substituted one or more times by halo, which aryl group is unsubstituted or substituted one or more times by aryl, heterocyclyl, aryloxy, aryl$C_{1-6}$alkoxy, amino, $C_{1-6}$alkylamino, di($C_{1-6}$alkyl)amino, aryl$C_{1-6}$alkyl, hydroxy, $C_{1-6}$alkenoxy, $C_{1-6}$alkoxy, halo, or $C_{1-6}$alkyl, which $C_{1-6}$alkyl may be substituted one or more times by halo, and wherein the aryl group is linked to said ring by a single bond or is benzo-condensed therewith.

Suitably, B represents a $C_{4-8}$ saturated or unsaturated ring, which ring is unsubstituted or substituted one or more times by $C_{1-6}$alkyl, $C_{1-6}$alkoxy, $C_{1-6}$alkenoxy, aryl, aryloxy, hydroxy, oxo, halo, amino, $C_{1-6}$alkylamino, di($C_{1-6}$alkyl) amino, and $C_{1-6}$alkylamido, which $C_{1-6}$alkyl or $C_{1-6}$alkoxy groups are unsubstituted or substituted one or more times by halo, which aryl group is unsubstituted or substituted one or more times by aryl, heterocyclyl, aryloxy, aryl$C_{1-6}$alkoxy, amino, $C_{1-6}$alkylamino, di($C_{1-6}$alkyl)amino, aryl$C_{1-6}$alkyl, hydroxy, $C_{1-6}$alkenoxy, $C_{1-6}$alkoxy, halo, or $C_{1-6}$alkyl, which $C_{1-6}$alkyl may be substituted one or more times by halo, and wherein the aryl group is linked to said ring by a single bond or is benzo-condensed therewith, provided that any benzo-condensed aryl group is substituted at least once.

Favourably, B represents a $C_{6-7}$ unsaturated ring or a $C_{5-7}$ saturated ring, which ring is unsubstituted or substituted by oxo, hydroxy, $C_{1-6}$alkenoxy, or $C_{1-6}$alkoxy, and is benzo-condensed with one unsubstituted or substituted aryl group, wherein suitable substituents for said aryl group are $C_{1-6}$alkoxy, $C_{1-6}$alkyl, halo, aryl, aryl$C_{1-6}$alkoxy, and hydroxy.

More favourably, B is cyclohexyl, cyclohexenyl, cyclopentyl, cycloheptenyl, or cycloheptyl, either unsubstituted or substituted with hydroxy, oxo, methoxy, or 2-propen-1-oxy, and is benzo-condensed with either phenyl or naphthyl, wherein said phenyl and naphthyl groups are either unsubstituted or substituted with methoxy, methyl, chloro, fluoro, phenyl, bromo, benzyloxy, or hydroxy.

Preferably, B is cycloheptyl either unsubstituted or substituted with hydroxy, or oxo, and is benzo-condensed with phenyl, said phenyl group being either unsubstituted or substituted with methyl, chloro, fluoro, bromo, or methoxy. More preferably, B is cycloheptyl substituted with hydroxy, and is benzo-condensed with phenyl, said phenyl group being either unsubstituted or substituted with methyl, bromo, or methoxy.

Most preferably, B is cycloheptyl substituted with hydroxy, and is benzo-condensed with phenyl, said phenyl group being substituted with methyl.

Thus, examples of B are 2,3-dihydroindene, 1,2,3,4-tetrahydronaphthalene, 1,2-dihydronaphthalene, 6,7,8,9-tetrahydro-5H-benzocycloheptene, unsubstituted or substituted by oxo, hydroxy, alkoxy, amino, dialkyamino, and/or alkylamido; or phenylcyclopentyl, phenylcyclohexyl, or phenylcycloheptyl, unsubstituted or substituted by oxo, hydroxy, alkoxy, amino, dialkyamino, or alkylamido.

"Aryl" as used herein includes $C_{5-10}$ aryl groups, particularly phenyl and naphthyl. $C_{1-6}$alkyl groups may be linear or branched and are preferably $C_{1-2}$alkyl groups, more preferably methyl. "Halo" includes chloro, bromo, and fluoro groups, especially fluoro and bromo. "Heterocyclyl" as used herein includes saturated and unsaturated heterocyclic rings.

Examples of compounds in accordance with the present invention are:

(±)-7-[(4-Phenylpiperidin-1-yl)methyl]-6,7,8,9-tetrahydro-5H-benzocyclohepten-5-one;

(±)-7-cis-[(4-Phenylpiperidin-1-yl)methyl]-6,7,8,9-tetrahydro-5H-benzocyclohepten-5-ol;

(±)-2-[(4-Phenylpiperidin-1-yl)methyl]-1,2-dihydronaphthalene;

(±)-3-[(4-Phenylpiperidin-1-yl)methyl]-1-oxo-2H-3,4-dihydronaphthalene;

(R)-(−)-3-[(4-Phenylpiperidin-1-yl)methyl]-1-oxo-2H-3,4-dihydronaphthalene;

(±)-2-[(4-Phenylpiperidin-1-yl)methyl]-1,2,3,4-tetrahydro naphthalene;

(S)-(+)-3-[(4-Phenylpiperidin-1-yl)methyl]-1-oxo-2H-3,4-dihydronaphthalene;

(±)-3-[(4-Phenylpiperidin-1-yl)methyl]-1-hydroxy-2H-3,4-dihydronaphthalene;
(±)-1,2-Dihydro-2-[(4-phenylpiperidin-1-yl)methyl]phenanthren-4-(3H)-one;
1-(2,3-Dihydro-1H-inden-2-yl)-4-phenylpiperidine;
(±)-1-Methoxy-7-[(4-phenylpiperidin-1-yl)methyl]-6,7,8,9-tetrahydro-5H-benzocyclohepten-5-ol;
(±)-3-Methoxy-7-[(4-phenylpiperidin-1-yl)methyl]-6,7,8,9-tetrahydro-5H-benzocyclohepten-5-ol;
(±)-1-Methoxy-7-[(4-phenylpiperidin-1-yl)methyl]-6,7,8,9-tetrahydro-5H-benzocyclohepten-5-one;
(±)-3-Methoxy-7-[(4-phenylpiperidin-1-yl)methyl]-6,7,8,9-tetrahydro-5H-benzocyclohepten-5-one;
(±)-cis-5-Methoxy-7-[(4-phenylpiperidin-1-yl)methyl]-6,7,8,9-tetrahydro-5H-benzocycloheptene;
(±)-trans-5-Methoxy-7-[(4-phenylpiperidin-1-yl)methyl]-6,7,8,9-tetrahydro-5H-benzocycloheptene;
2,3-Dihydro-2-[(4-phenylpiperidin-1-yl)methyl]indene;
N-(6,7,8,9-Tetrahydro-5H-benzocyclohepten-7-yl)-4-phenylpiperidine;
(±)-cis-1-Methyl-7-[[4-(2-methylphenyl)piperidin-1-yl]methyl]-6,7,8,9-tetrahydro-5H-benzocyclohepten-5-ol;
(±)-1,3-Dimethyl-7-[(4-phenylpiperidin-1-yl)methyl]-6,7,8,9-tetrahydro-5H-benzocyclohepten-5-ol;
(±)-cis-7-[[4-(2-Methoxyphenyl)piperidin-1-yl]methyl]-6,7,8,9-tetrahydro-5H-benzocyclohepten-5-ol;
(±)-cis-3-Chloro-7-[(4-phenylpiperidin-1-yl)methyl]-6,7,8,9-tetrahydro-5H-benzocyclohepten-5-ol;
(±)-1-Chloro-7-[(4-phenylpiperidin-1-yl)methyl]-6,7,8,9-tetrahydro-5H-benzocyclohepten-5-ol;
(±)-7-[[4-(2-Hydroxyphenyl)piperidin-1-yl]methyl]-6,7,8,9-tetrahydro-5H-benzocyclohepten-5-ol;
(±)-cis-7-[[4-(3-Fluorophenyl)piperidin-1-yl]methyl]-6,7,8,9-tetrahydro-5H-benzocyclohepten-5-ol;
(±)-cis-7-[[4-(2-Methylphenyl)piperidin-1-yl]methyl]-6,7,8,9-tetrahydro-5H-benzocyclohepten-5-ol;
(±)-cis-1-Methyl-7-[(4-phenylpiperidin-1-yl)methyl]-6,7,8,9-tetrahydro-5H-benzocyclohepten-5-ol;
(±)-cis-7-[[4-(4-Benzyloxyphenyl)piperidin-1-yl]methyl]-6,7,8,9-tetrahydro-5H-benzocyclohepten-5-ol;
(±)-cis-7-[[4-(3-Bromophenyl)piperidin-1-yl]methyl]-6,7,8,9-tetrahydro-5H-benzocyclohepten-5-ol;
(±)-1-Fluoro-7-[(4-phenylpiperidin-1-yl)methyl]-6,7,8,9-tetrahydro-5H-benzocyclohepten-5-ol;
(±)-7-[[4-(4-Fluorophenyl)piperidin-1-yl]methyl]-6,7,8,9-tetrahydro-5H-benzocyclohepten-5-ol;
(±)-7-[[4-(3,5-Dimethoxyphenyl)piperidin-1-yl]methyl]-6,7,8,9-tetrahydro-5H-benzocyclohepten-5-ol;
(±)-cis-1-Phenyl-7-[(4-phenylpiperidin-1-yl)methyl]-6,7,8,9-tetrahydro-5H-benzocyclohepten-5-ol;
(±)-7-[[4-(2-Chlorophenyl)piperidin-1-yl]methyl]-6,7,8,9-tetrahydro-5H-benzocyclohepten-5-ol;
(±)-cis-1-Bromo-7-[(4-phenylpiperidin-1-yl)methyl]-6,7,8,9-tetrahydro-5H-benzocyclohepten-5-ol;
(±)-1-Benzyloxy-7-[(4-phenylpiperidin-1-yl)methyl]-6,7,8,9-tetrahydro-5H-benzocyclohepten-5-ol;
(±)-cis-1-Methyl-7-[[4-(3-fluorophenyl)piperidin-1-yl]methyl]-6,7,8,9-tetrahydro-5H-benzocyclohepten-5-ol;
(±)-cis-1-Methoxy-7-[[4-(2-methylphenyl)piperidin-1-yl]methyl]-6,7,8,9-tetrahydro-5H-benzocyclohepten-5-ol;
(±)-trans-1-Methoxy-7-[[4-(2-methylphenyl)piperidin-1-yl]methyl]-6,7,8,9-tetrahydro-5H-benzocyclohepten-5-ol;
(±)-cis-1-Methoxy-7-[[4-(3-fluorophenyl)piperidin-1-yl]methyl]-6,7,8,9-tetrahydro-5H-benzocyclohepten-5-ol;
(±)-trans-1-Methoxy-7-[[4-(3-fluorophenyl)piperidin-1-yl]methyl]-6,7,8,9-tetrahydro-5H-benzocyclohepten-5-ol;
(±)-cis-1-Hydroxy-7-[(4-phenylpiperidin-1-yl)methyl]-6,7,8,9-tetrahydro-5H-benzocyclohepten-5-ol;
(±)-4-Methoxy-7-[(4-phenylpiperidin-1-yl)methyl]-6,7,8,9-tetrahydro-5H-benzocyclohepten-5-ol;
(±)-1,3-Dimethyl-7-[(4-phenylpiperidin-1-yl)methyl]-6,7,8,9-tetrahydro-5H-benzocyclohepten-5-one;
(±)-7-[[4-(2-Methoxyphenyl)piperidin-1-yl]methyl]-6,7,8,9-tetrahydro-5H-benzocyclohepten-5-one;
(±)-3-Chloro-7-[(4-phenylpiperidin-1-yl)methyl]-6,7,8,9-tetrahydro-5H-benzocyclohepten-5-one;
(±)-1-Chloro-7-[(4-phenylpiperidin-1-yl)methyl]-6,7,8,9-tetrahydro-5H-benzocyclohepten-5-one;
(±)-7-[[4-(2-Hydroxyphenyl)piperidin-1-yl]methyl]-6,7,8,9-tetrahydro-5H-benzocyclohepten-5-one;
(±)-1-Methyl-7-[(4-phenylpiperidin-1-yl)methyl]-6,7,8,9-tetrahydro-5H-benzocyclohepten-5-one;
(±)-7-[[4-(2-Methylphenyl)piperidin-1-yl]methyl-6,7,8,9-tetrahydro-5H-benzocyclohepten-5-one;
(±)-7-[(4-Phenylpiperidin-1-yl)methyl]-6,7-dihydro-5H-benzocycloheptene;
7-[(4-Phenylpiperidin-1-yl)methyl]-6,7,8,9-tetrahydro-5H-benzocycloheptene;
7-[[4-(2-Methylphenyl)piperidin-1-yl]methyl]-6,7,8,9-tetrahydro-5H-benzocycloheptene;
(±)-cis-5-Allyloxy-7-[(4-phenylpiperidin-1-yl)methyl]-6,7,8,9-tetrahydro-5H-benzocycloheptene;
(±)-trans-7-[(4-Phenylpiperidin-1-yl)methyl]-6,7,8,9-tetrahydro-5H-benzocyclohepten-5-ol;
(±)-cis-1-Methoxy-7-[(4-phenylpiperidin-1-yl)methyl]-6,7,8,9-tetrahydro-5H-benzocyclohepten-5-ol;
(±)-trans-1-Methoxy-7-[(4-phenylpiperidin-1-yl)methyl]-6,7,8,9-tetrahydro-5H-benzocyclohepten-5-ol;
(+)-1-Methoxy-7-[(4-phenylpiperidin-1-yl)methyl]-6,7,8,9-tetrahydro-5H-benzocyclohepten-5-one;
(−)-1-Methoxy-7-[(4-phenylpiperidin-1-yl)methyl]-6,7,8,9-tetrahydro-5H-benzocyclohepten-5-one;
(+)-cis-1-Methoxy-7-[(4-phenylpiperidin-1-yl)methyl]-6,7,8,9-tetrahydro-5H-benzocyclohepten-5-ol;
(−)-cis-1-Methoxy-7-[(4-phenylpiperidin-1-yl)methyl]-6,7,8,9-tetrahydro-5H-benzocyclohepten-5-ol;
(+)-trans-1-Methoxy-7-[(4-phenylpiperidin-1-yl)methyl]-6,7,8,9-tetrahydro-5H-benzocyclohepten-5-ol;
(−)-trans-1-Methoxy-7-[(4-phenylpiperidin-1-yl)methyl]-6,7,8,9-tetrahydro-5H-benzocyclohepten-5-ol;
[4-(2-Methylphenyl)-N-(6,7,8,9-tetrahydro-5H-benzocyclohepten-7-yl)]piperidine;
(−)-cis-1-Methyl-7-[[4-(2-methylphenyl)piperidin-1-yl]methyl]-6,7,8,9-tetrahydro-5H-benzocyclohepten-5-ol, and;
(+)-cis-1-Methyl-7-[[4-(2-methylphenyl)piperidin-1-yl]methyl]-6,7,8,9-tetrahydro-5H-benzocyclohepten-5-ol.

Especially preferred compounds are:
(±)-cis-1-Methyl-7-[[4-(2-methylphenyl)piperidin-1-yl]methyl]-6,7,8,9-tetrahydro-5H-benzocyclohepten-5-ol;
(±)-cis-7-[[4-(3-Fluorophenyl)piperidin-1-yl]methyl]-6,7,8,9-tetrahydro-5H-benzocyclohepten-5-ol;
(±)-cis-7-[[4-(2-Methylphenyl)piperidin-1-yl]methyl]-6,7,8,9-tetrahydro-5H-benzocyclohepten-5-ol;
(±)-7-[[4-(2-Chlorophenyl)piperidin-1-yl]methyl]-6,7,8,9-tetrahydro-5H-benzocyclohepten-5-ol;

(±)-cis-1-Bromo-7-[(4-phenylpiperidin-1-yl)methyl]-6,7,8,9-tetrahydro-5H-benzocyclohepten-5-ol;
(±)-cis-1-Methyl-7-[[4-(3-fluorophenyl)piperidin-1-yl]methyl]-6,7,8,9-tetrahydro-5H-benzocyclohepten-5-ol;
(−)-cis-1-Methoxy-7-[(4-phenylpiperidin-1-yl)methyl]-6,7,8,9-tetrahydro-5H-benzocyclohepten-5-ol, and;
(−)-cis-1-Methyl-7-[[4-(2-methylphenyl)piperidin-1-yl]methyl]-6,7,8,9-tetrahydro-5H-benzocyclohepten-5-ol.

In accordance with another aspect of the invention, there is provided a process for the preparation of a compound in accordance with the invention, which process comprises:—
1) where A in formula I is a bond (formula I'),
a). reacting a ketone of formula II with an amine of formula III under reductive amination conditions, such as NaCNBH$_3$ in methanol or acetonitrile (Lane, *Synthesis*, 135, 1975),

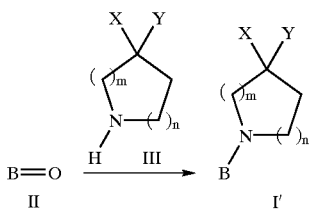

wherein B, m, n, X and Y are as defined in formula I, or
b). transforming an alcohol of formula IV into a suitable leaving group (e.g. methanesulfonate, p-toluenesulfonate or bromide) and subsequent reaction with an amine of formula III,

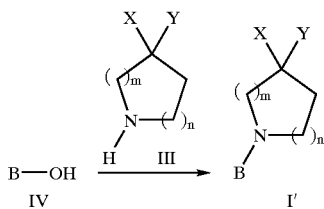

wherein B, m, n, X and Y are as defined in formula I; or
2) where A in formula I is a group —(CR$_{pa}$R$_{pb}$)$_p$— and p is 1 and R$_{pa}$ and R$_{pb}$ are both hydrogen (formula I"),
c) reacting a carboxylic acid of formula V with an amine of formula III via formation of an acyl halide or by direct reaction with a coupling agent, such as dicyclohexylcarbodiimide/1-hydroxybenzotriazole, N-ethyl-N'-(3-dimethylaminopropyl)carbodiimide/1-hydroxybenzotriazole or O-benzotriazol-1-yl-N,N,N',N'-tetramethyluronium hexafluorophosphate, and thereafter reducing the resulting amide of formula VI using a metal hydride or borane-based reagent,

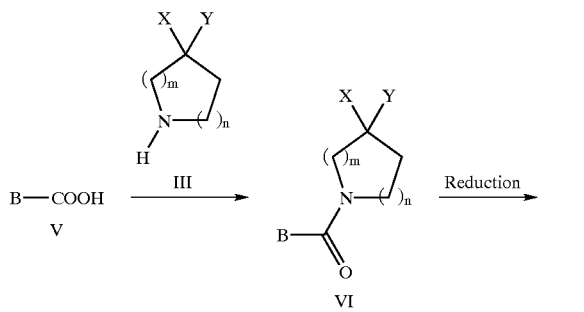

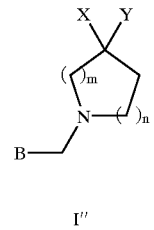

wherein B, m, n, X and Y are as defined in formula I, or
d) reducing a carboxylic acid of formula V to an alcohol of formula VII (Pelter Smith, Brown, *Borane Reagents*; Academic Press: London, 1988), and reacting said alcohol with an amine of formula III according to method b) above,

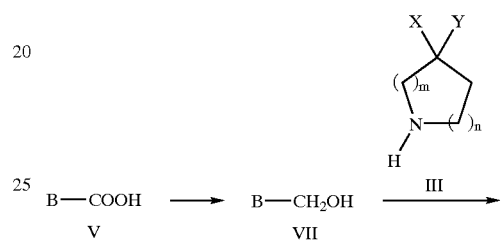

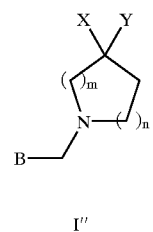

wherein B, m, n, X and Y are as defined in formula I, or
e) oxidizing an alcohol of formula VII to an aldehyde of formula VIII, using for example MnO$_2$, PDC or DMSO/oxalyl chloride (Swern, *J. Org. Chem.*, 43, 2480, 1978) and reacting said aldehyde with an amine of formula III under reductive amination conditions, according to method a) above,

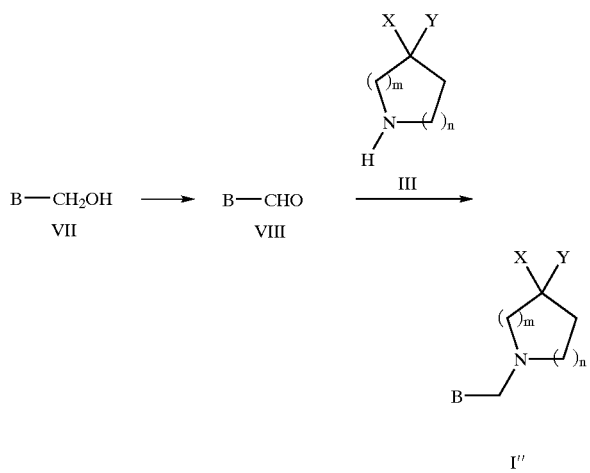

wherein B, m, n, X and Y are as defined in formula I; or
3) where A in formula I is a group —(CR$_{pa}$R$_{pb}$)$_p$— and p is 1, R$_{pa}$ is a C$_{1-6}$ alkyl group and R$_{pb}$ is hydrogen (formula I'"), f) reacting a carboxylic acid or a derivative thereof of formula V with an organometallic compound of formula $R_{pa}M$ wherein M represents a metal such as Li, Mg, Cu or Zn, e.g. alkyllithium derivatives, Grignard reagents, lithium dialkylcuprates or dialkylzinc derivatives (Trost, Fleming, *Comprehensive Organic Synthesis*; Pergamon Press: Oxford, 1991; Vol. III), and thereafter reacting the resulting carbonylic compound IX with an amine of formula III under reductive amination conditions, according to method a) above,

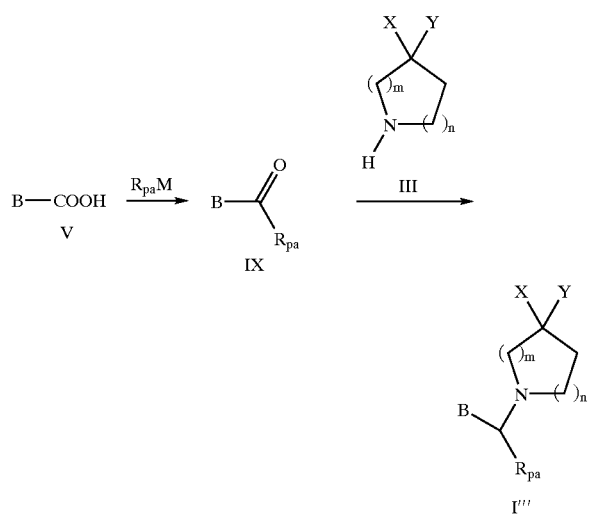

wherein B, $R_{pa}$, m, n, X and Y are as defined in formula I; or 4) where A in formula I is a group —$(CR_{pa}\ R_{pb})_p$— and p is 1, and $R_{pa}$ and $R_{2pb}$ are both $C_{1-6}$ alkyl groups (formula I''''), g) reacting a carbonylic compound of formula IX with an organometallic of formula $R_{pb}M$, wherein M represents a metal such as Li or Mg, e.g. alkyllithium derivatives or Grignard reagents, and coupling the resulting alcohol of formula X with an amine of formula III according to method b) above

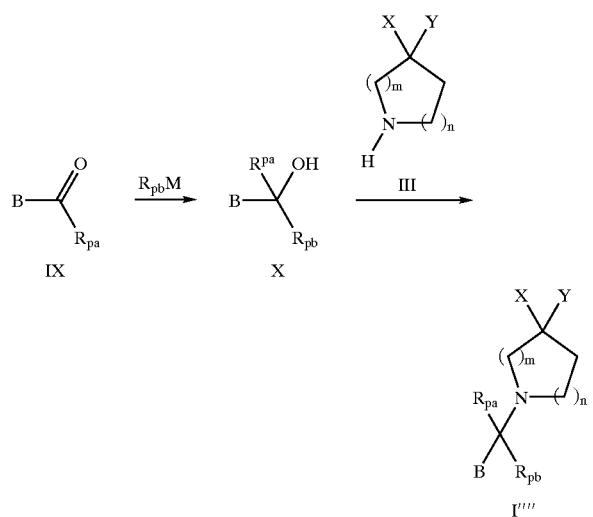

wherein B, $R_{pa}$, $R_{pb}$, m, n, X and Y are as defined in formula I.

Compounds of formula II, IV and V are either known compounds or may be prepared from known compounds with known methods (Hacksell, *J. Med. Chem.*, 24, 429, 1981, Murthy, *Tetrahedron*, 38, 2831, 1982, Bowman, *Tetrahedron*, 48, 4027, 1992).

Compounds of formula III are either known compounds or may be prepared from known compounds with known methods (Comins, *J. Org. Chem.*, 47, 4315, 1982).

Said compounds in accordance with the invention may be prepared in the form of salts or hydrates.

Suitable salts are pharmaceutically acceptable salts.

Suitable hydrates are pharmaceutically acceptable hydrates.

Administration of a compound in accordance with the invention may be by way of oral, sublingual, transdermal or parenteral administration.

An effective amount of the compound of the invention will depend on factors such, for example, as the nature and severity of the disorder(s) being treated and on the weight of the mammal. However, a unit does will normally contain 0.1 to 50 mg, for example 0.5 to 10 mg, of the compound. Unit doses will normally be administered once or more than once a day, for example 2, 3, or 4 times a day, more usually 1 to 3 times a day, such that the total daily dose is normally in the range, for a 70 kg adult of 0.1 to 50 mg, for example 0.1 to 5 mg, that is in the range of approximately 0.001 to 1 mg/kg/day, more usually 0.005 to 0.2 mg/kg/day.

For oral or parenteral administration, it is greatly preferred that the compound is administered in the form of a unit dose composition, such as a unit dose oral or parenteral composition.

Such compositions are prepared by admixture and are suitably adapted for oral or parenteral administration, and as such may be in the form of tablets, capsules, oral preparations, powders, granules, lozenges, reconstitutable powders, injectable and liquid infusible solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers include cellulose, mannitol, lactose and other similar agents.

Suitable disintegrants include starch, polyvinylpyrrolidone and starch derivatives such as sodium starch glycolate.

Suitable lubricants include, for example, magnesium stearate.

Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms may be prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition may be frozen after filling into the vial and the water removed under vacuum.

Parenteral suspensions are prepared in substantially the same manner except that the compound may be suspended in the vehicle instead of being dissolved and sterilised by exposure to ethylene oxide before suspending in the sterile vehicle. Advantageously, a surfactant or wetting agent may be included in the composition to facilitate uniform distribution of the compound of the invention.

As is common practice, the compositions will usually be accompanied by written or printed directions for use in the treatment concerned.

Accordingly, in yet another aspect of the present invention there is also provided a pharmaceutical composition comprising a compound of formula I, or a pharmaceutically acceptable salt thereof or a pharmaceutically acceptable hydrate thereof, and a pharmaceutically acceptable carrier.

Preparation 1

(±)-4-Oxo-1,2,3,4-tetrahydro-2-naphthoic acid 100 mL (0.425 mol) of diethyl benzylmalonate were added dropwise to a stirred suspension of 28 g (0.7 mol) of NaH (60% dispersion in mineral oil) in 550 mL of absolute ethanol at room temperature. The reaction mixture was refluxed 2 h, then cooled to 50° C. and 47.1 mL (0.425 mol) of ethyl bromoacetate were added dropwise. The reaction mixture was refluxed 2 h, then quenched with 150 mL of water; a solution of 140 g (3.5 mol) of NaOH in 400 mL of water was added and the mixture was heated to reflux for 1 h. EtOH was removed in vacuo, the aqueous solution was washed with $Et_2O$ and then carefully brought to acidic pH with 350 mL of 37% HCl and extracted with AcOEt. The solvent was removed in vacuo and the resulting residue was heated to 180° C. for 30 min. After cooling to room temperature, 100 mL of 95% $H_2SO_4$ were added and the reaction mixture stirred for 2 h, then it was poured onto 500 g of crushed ice and extracted with $Et_2O$. The organic phase was dried and the solvent removed in vacuo. The resulting residue was taken up in $Et_2O$, washed with 40% NaOH solution then brought to acidic pH with 37% HCl and extracted with $Et_2O$. The organic phase was dried and the solvent removed in vacuo. The resulting solid residue was triturated with $Et_2O$, filtered and dried yielding 15 g of the title compound, used without further purification. m.p.= 146–147° C. IR ($cm^{-1}$): 2924, 1692, 1600; NMR (300 MHz, DMSO, δ ppm): 12.6–12.5 (bs, 1H); 7.9 (d, 1H); 7.6–7.5 (m, 1H); 7.4–7.3 (m, 2H); 3.3–3.1 (m, 3H); 2.7 (m, 2H). MS (m/z): 191.1 ($MH^+$).

Preparation 2

(R)-(−)-4-Oxo-1,2,3,4-tetrahydro-2-naphthoic acid

A solution of 7.436 g (55 mmol) of (−)-α-ethylbenzylamine in 100 mL of MeOH was added to a solution of 10.5 g (55 mmol) of (±)-4-oxo-1,2,3,4-tetrahydro-2-naphthoic acid in 100 mL of MeOH. The solvent was removed in vacuo, and the residue was dissolved in 200 mL of AcOEt. The less soluble diastereoisomeric salt crystallised on standing. The salt was then recrystallised from AcOEt up to a constant optical activity, yielding 3.5 g of salt, which was transformed into the free acid by dissolving it in 6N HCl, extracting with $Et_2O$ and evaporating the solvent, yielding 2 g of the title compound. $[α]^{20}_D$=−39.3 (c=1.5, MeOH). IR, NMR and m.p. matched those of the racemate.

Preparation 3

(S)-(+)-4-Oxo-1,2,3,4-tetrahydro-2-naphthoic acid

The mother liquors obtained from the first crystallisation of Preparation 2 were evaporated to dryness. The residue was dissolved in 6N HCl, extracted with $Et_2O$ and evaporated to dryness, yielding 5.34 g of free acid which were treated with 3.79 g of (+)-α-ethylbenzylamine and worked up as described in Preparation 2, yielding 1.8 g of the title compound. $[α]^{20}_D$=+39.48 (c=1.5, MeOH). IR, NMR and m.p. matched those of the racemate.

Preparation 4

2,3-Dihydro-2-[(4-phenylpiperidin-1-yl)carbonyl]-1H-indene 750 mg (4.6 mmol) of 2,3-dihydro-1H-inden-2-carboxylic acid (prepared as described in Hacksell, *J. Med. Chem.*, 24, 429, 1981) were dissolved in 15 mL of $CH_2Cl_2$ and 0.65 mL (7.4 mmol) of oxalyl chloride were added dropwise at 0° C. under a nitrogen atmosphere. The solution was allowed to warm to room temperature in 2 h, then the solvent was removed in vacuo. The resulting acyl chloride was dissolved in 10 mL of $CH_2Cl_2$ and added to a solution of 909 mg (4.6 mmol) of 4-phenylpiperidine hydrochloride and 1.9 mL (13.8 mmol) of triethylamine in 15 mL of $CH_2Cl_2$ at 0° C. The reaction mixture was allowed to warm to room temperature overnight, then water was added and the organic phase was washed with 5% HCl and dried. The solvent was removed in vacuo and the resulting crude product was purified by flash chromatography, eluting with a mixture $Et_2O$/Petroleum ether 7:3, yielding 630 mg of the title compound. IR ($cm^{-1}$)=2944, 1636, 1494. NMR (300 MHz, $CDCl_3$, δ ppm): 7.35 (m, 2H); 7.25–7.1 (m, 7H); 4.85 (m, 1H); 4.15 (m, 1H); 3.55 (m, 1H); 3.4–3.3 (m, 2H); 3.3–3.1 (m, 3H); 2.85–2.6 (m, 2H); 2.0–1.9 (m, 2H); 1.75.1.6 (m, 2H). MS (m/z): 306.0 ($MH^+$).

Compounds of formula VI and described in Table I were obtained following the procedure described in Preparation 4.

eluting with a mixture $CH_2Cl_2$/MeOH 9:1 respectively, yielding 0.41 g of the title compound. m.p.=134–135° C.

TABLE 1

VI

| Prep n° | Name | B | X | Y | m | n | m.p. (° C.) | IR (cm$^{-1}$) | MS (m/z) (MH$^+$) | $[α]^{20}_D$ |
|---|---|---|---|---|---|---|---|---|---|---|
| 5 | (±)-3-[(4-Phenylpiperidin-1-yl)carbonyl]-1-oxo-2H-3,4-dihydronaphthalene | | Ph | H | 2 | 1 | 118–119 | 2934, 1688, 1642 | 334.3 | — |
| 6 | (S)-(+)-3-[(4-Phenylpiperidin-1-yl)carbonyl]-1-oxo-2H-3,4-dihydronaphthalene | | Ph | H | 2 | 1 | 118–120 | 2930, 1688, 1642 | 334.4 | +43.2 c = 1, MeOH |
| 7 | (R)-(-)-3-[(4-Phenylpiperdin-1-yl)carbonyl]-1-oxo-2H-3,4-dihydronaphthalene | | Ph | H | 2 | 1 | 118–119 | 2930, 1688, 1644 | 334.4 | −41.2 c = 1, MeOH |
| 8 | (±)-2-[(4-Phenylpiperidin-1-yl)carbonyl]-1,2,3,4-tetrahydronaphthalene | | Ph | H | 2 | 1 | 90–91 | 2926, 1626, 1442 | 320.2 | — |
| 9 | (±)-1,2-Dihydro-2-[(4-phenylpiperidin-1-yl)carbonyl]phenanthren-4-(3H)-one | | Ph | H | 2 | 1 | — | — | — | — |

Preparation 10

(±)-6,7,8,9-tetrahydro-5H-benzocyclohepten-5-one-7-carboxylic acid

A suspension of 0.7 g (3 mmol) of ethyl (±)-6,7,8,9-tetrahydro-5H-benzocyclohepten-5-one-7-carboxylate (prepared as described in Bowman, *Tetrahedron*, 48, 4027, 1992) in 2 mL of 2N NaOH (4 mmol) was refluxed for 2 h, then cooled and extracted with Et$_2$O. The aqueous layer was brought to acidic pH with 10% HCl, the precipitate formed was redissolved in Et$_2$O and the organic phase was washed with water and dried. The solvent was removed in vacuo and the resulting residue was purified by flash chromatography, Preparation 11

(±)-7-[(4-Phenylpiperidin-1-yl)carbonyl]-6,7,8,9-tetrahydro-5H-benzocyclohepten-5-one To a solution of 0.3 g (1.47 mmol) of (±)-6,7,8,9-tetrahydro-5H-benzocyclohepten-5-one-7-carboxylic acid in 5 mL of CH$_2$Cl$_2$ were added, at 0° C., 0.27 mL (3.69 mmol) of SOCl$_2$ and the solution was warmed at 50° C. for 20 min. The solvent and the excess SOCl$_2$ were removed in vacuo and the resulting residue was redissolved in 5 mL of CH$_2$Cl$_2$. 0.24 g (1.47 mmol) of 4-phenylpiperidine and 0.2 mL (1.47 mmol) of triethylamine dissolved in 5 mL of CH$_2$Cl$_2$ were added at room temperature to this solution; the stirring was continued overnight, then the solvent was removed in vacuo and the residue was taken up in AcOEt; the organic phase was washed successively with 10% NaOH, 10% HCl and water, the solvent was removed in vacuo yielding 0.49 g of the title compound as an oil which was used without further purification.

Preparation 12

2-Methylphenethyl alcohol methanesulfonate 10 g (0.0734 mol) of 2-methylphenethyl alcohol were dissolved in 200 mL of dry $CH_2Cl_2$ under a nitrogen atmosphere; the solution was cooled to 5° C., 16.4 mL (0.1175 mol) of triethylamine were added, followed by a solution of 9.1 mL (0.1175 mol) of methanesulfonyl chloride in 100 mL of dry $CH_2Cl_2$, keeping the temperature below 15° C. The reaction mixture was allowed to warm to room temperature in 2 h, then 250 mL of water were added, the organic phase was collected and the solvent was removed in vacuo. The resulting oil was taken up in $Et_2O$ and washed with 1N HCl and successively with saturated $NaHCO_3$ solution, the solvent was removed in vacuo, yielding 14.5 g of the title product which was used without further purification.

IR, $^1H$ nmr spectra and mass spectra were consistent with the assigned structure.

Preparation 13

Diethyl (2-methyl)phenethyl malonate 33.9 mL (0.223 mol) of diethyl malonate were added, under a nitrogen atmosphere and at room temperature, to a solution of sodium ethoxide (prepared in situ by dissolving 2.6 g (0.0151 mol) of Na in 80 mL of absolute EtOH). After 30 min, 14.5 g (0.0677 mol) of 2-methylphenethyl alcohol methanesulfonate dissolved in 40 mL of abs. EtOH were added dropwise and the resulting solution was heated to reflux for 3 h. EtOH was removed in vacuo, the residue was taken up in water and extracted with $Et_2O$. The organic phase was washed successively with 10% HCl and brine, dried and the solvent was removed in vacuo. The excess diethyl malonate was removed by distillation under reduced pressure. The resulting oil (15.6 g) was used without further purification.

IR, $^1H$ nmr spectra and mass spectra were consistent with the assigned structure.

Preparation 14

Diethyl 2-(t-butoxycarbonylmethyl)-2-(2-methyl) phenethyl malonate

A solution of 7.7 g (0.0277 mol) of diethyl (2-methyl) phenethyl malonate in 70 ml of dry THF were added dropwise, under a nitrogen atmosphere at room temperature, to a suspension of 1.4 g (0.036 mol) of NaH (60% dispersion in mineral oil) in 160 mL of dry THF. The reaction mixture was stirred for 30 min, then 5.3 mL (0.036 mol) of t-butyl bromoacetate were added dropwise. After 3 h the reaction mixture was quenched with water (at 0° C.) and extracted with $Et_2O$. The organic phase was dried, the solvent was removed in vacuo and the residue was purified by flash chromatography, eluting with a mixture Hexane/$Et_2O$ 8:2, yielding 9.3 g of the title compound.

IR, $^1H$ nmr spectra and mass spectra were consistent with the assigned structure.

Preparation 15

Diethyl 2-carboxymethyl-2-(2-methyl)phenethyl malonate 18.7 g (0.0476 mol) of diethyl 2-(t-butoxycarbonylmethyl)-2-(2-methyl)phenethyl malonate were dissolved in 40 mL of trifluoroacetic acid and stirred 1 h at room temperature. Trifluoroacetic acid was removed in vacuo, the residue was taken up in water and extracted with $Et_2O$. The organic phase was dried and the solvent was removed in vacuo, yielding 16.8 g of the title compound which was used without further purification.

IR, $^1H$ nmr spectra and mass spectra were consistent with the assigned structure.

Preparation 16

(±)-1-Methyl-5-oxo-6,7,8,9-tetrahydro-5H-benzocycloheptene-7-carboxylic acid 16.8 g (0.0499 mol) of diethyl 2-carboxymethyl-2-(2-methyl)phenethyl malonate were dissolved in 120 mL of $CH_2Cl_2$ under a nitrogen atmosphere. The solution was cooled to 5° C. and 19 mL (0.1498 mol) of oxalyl chloride were added dropwise. After 3 h the volatiles were removed in vacuo, the resulting oil was dissolved in 200 mL of $CH_2Cl_2$ and this solution was added dropwise, at 0° C. and under inert atmosphere, to a suspension of 26.6 g (0.1996 mol) of $AlCl_3$ in 300 mL of $CH_2Cl_2$. The resulting suspension was vigorously stirred overnight, during which time it was allowed to warm to room temperature. Water was added, followed by 1N HCl up to pH 1. The layers were separated, the organic phase was dried and the solvent was removed in vacuo. The resulting crude product was taken up in dioxane (60 mL) and 6N HCl (200 mL) and heated to reflux for 6 h. After cooling, water was added and the reaction mixture was extracted with $Et_2O$. The organic phase was dried, the solvent was removed in vacuo and the resulting crude product was purified by flash chromatography eluting with $Et_2O$, yielding 5.9 g of the title product.

IR, $^1H$ nmr spectra and mass spectra were consistent with the assigned structure.

The following compounds were obtained according to procedures described in Preparations 12–16:
(±)-1,3-Dimethyl-5-oxo-6,7,8,9-tetrahydro-5H-benzocycloheptene-7-carboxylic acid;
(±)-3-Chloro-5-oxo-6,7,8,9-tetrahydro-5H-benzocycloheptene-7-carboxylic acid;
(±)-1-Chloro-5-oxo-6,7,8,9-tetrahydro-5H-benzocycloheptene-7-carboxylic acid;
(±)-1-Fluoro-5-oxo-6,7,8,9-tetrahydro-5H-benzocycloheptene-7-carboxylic acid, and;
(±)-1-Bromo-5-oxo-6,7,8,9-tetrahydro-5H-benzocycloheptene-7-carboxylic acid.

IR, $^1H$ nmr spectra and mass spectra for all the above compounds were consistent with the assigned structures.

Preparation 17

(±)-1-Methoxy-5-oxo-6,7,8,9-tetrahydro-5H-benzocycloheptene-7-carboxylic acid

The title compound was obtained following procedure described in Preparation 10.

IR and $^1H$ nmr spectra were consistent with the assigned structure.

Preparation 18

(±)-4-Methoxy-5-oxo-6,7,8,9-tetrahydro-5H-benzocycloheptene-7-carboxylic acid

The title compound was obtained following procedure assigned in Preparation 10.

IR and $^1H$ nmr spectra were consistent with the assigned structure.

The following compounds were obtained according to procedure described in Preparation 4:
(±)-1-Methyl-7-[(4-phenylpiperidin-1-yl)carbonyl]-6,7,8,9-tetrahydro-5H-benzocyclohepten-5-one;

(±)-1-Methyl-7-[[4-(2-methylphenyl)piperidin-1-yl]
carbonyl]-6,7,8,9-tetrahydro-5H-benzocyclohepten-5-
one;

(±)-1-Methyl-7-[[4-(3-fluorophenyl)piperidin-1-yl]
carbonyl]-6,7,8,9-tetrahydro-5H-benzocyclohepten-5-
one;

(±)-1-Methoxy-7-[[4-(2-methylphenyl)piperidin-1-yl]
carbonyl]-6,7,8,9-tetrahydro-5H-benzocyclohepten-5-
one;

(±)-1-Methoxy-7-[[4-(3-fluorophenyl)piperidin-1-yl]
carbonyl]-6,7,8,9-tetrahydro-5H-benzocyclohepten-5-
one;

(±)-1,3-Dimethyl-7-[(4-phenylpiperidin-1-yl)carbonyl]-6,7,
8,9-tetrahydro-5H-benzocyclohepten-5-one;

(±)-3-Chloro-7-[(4-phenylpiperidin-1-yl)carbonyl]-6,7,8,9-
tetrahydro-5H-benzocyclohepten-5-one;

(±)-1-Chloro-7-[(4-phenylpiperidin-1-yl)carbonyl]-6,7,8,9-
tetrahydro-5H-benzocyclohepten-5-one;

(±)-1-Fluoro-7-[(4-phenylpiperidin-1-yl)carbonyl]-6,7,8,9-
tetrahydro-5H-benzocyclohepten-5-one;

(±)-1-Bromo-7-[(4-phenylpiperidin-1-yl)carbonyl]-6,7,8,9-
tetrahydro-5H-benzocyclohepten-5-one;

(±)-7-[[4-(2-Methoxyphenyl)piperidin-1-yl]carbonyl]-6,7,
8,9-tetrahydro-5H-benzocyclohepten-5-one;

(±)-7-[[4-(3-Fluorophenyl)piperidin-1-yl]carbonyl]-6,7,8,9-
tetrahydro-5H-benzocyclohepten-5-one;

(±)-7-[[4-(2-Methylphenyl)piperidin-1-yl]carbonyl]-6,7,8,
9-tetrahydro-5H-benzocyclohepten-5-one;

(±)-7-[[4-(4-Benzyloxyphenyl)piperidin-1-yl]carbonyl]-6,7,
8,9-tetrahydro-5H-benzocyclohepten-5-one;

(±)-7-[[4-(3-Bromophenyl)piperidin-1-yl]carbonyl]-6,7,8,
9-tetrahydro-5H-benzocyclohepten-5-one;

(±)-7-[[4-(4-Fluorophenyl)piperidin-1-yl]carbonyl]-6,7,8,9-
tetrahydro-5H-benzocyclohepten-5-one;

(±)-7-[[4-(3,5-Dimethoxyphenyl)piperidin-1-yl]carbonyl]-
6,7,8,9-tetrahydro-5H-benzocyclohepten-5-one;

(±)-7-[[4-(2-Chlorophenyl)piperidin-1-yl]carbonyl]-6,7,8,
9-tetrahydro-5H-benzocyclohepten-5-one;

(±)-1-Methoxy-7-[(4-phenylpiperidin-1-yl)carbonyl]-6,7,8,
9-tetrahydro-5H-benzocyclohepten-5-one, and;

(±)-4-Methoxy-7-[(4-phenylpiperidin-1-yl)carbonyl]-6,7,8,
9-tetrahydro-5H-benzocyclohepten-5-one.

IR, $^1$H nmr spectra and mass spectra for all the above compounds were consistent with the assigned structures.

Preparation 19

(±)-1-Phenyl-7-[(4-phenylpiperidin-1-yl)carbonyl]-
6,7,8,9-tetrahydro-5H-benzocyclohepten-5-one 0.6 g (1.54 mmol) of (±)-1-bromo-7-[(4-phenylpiperidin-1-yl)carbonyl]-6,7,8,9-tetrahydro-5H-benzocyclohepten-5-one were dissolved in 5 mL of toluene under a nitrogen atmosphere, then 54 mg (0.016 mmol) of Pd(PPh$_3$)$_4$ were added, followed by 1.5 mL of 2M Na$_2$CO$_3$ solution and 225 mg (1.85 mmol) of benzeneboronic acid dissolved in 2 mL of MeOH. The resulting heterogeneous mixture was refluxed for 8 h under vigorous stirring, then after cooling it was taken up with CH$_2$Cl$_2$ and water. 8 mL of 2M Na$_2$CO$_3$ solution and 1 mL of conc. NH$_4$OH were added, the organic layer was collected and dried, the solvent was removed in vacuo, yielding 660 mg of the title product which was used without further purification.

IR, $^1$H nmr spectra and mass spectra were consistent with the assigned structure.

Preparation 20

(±)-1-Hydroxy-7-[(4-phenylpiperidin-1-yl)
carbonyl]-6,7,8,9-tetrahydro-5H-benzocyclohepten-
5-one Under a nitrogen atmosphere, 2.2 mL (0.0234 mol) of BBr$_3$ were added to 20 mL of CH$_2$Cl$_2$, then 1.47 g (0.0039 mol) of (±)-1-methoxy-7-[(4-phenylpiperidin-1-yl)carbonyl]-6,7,8,9-tetrahydro-5H-benzocyclohepten-5-one dissolved in 25 mL of CH$_2$Cl$_2$ were added dropwise at room temperature. The reaction mixture was stirred for 2 h, then it was poured onto 25 g of crushed ice, basified with conc. NH$_4$OH and extracted with CH$_2$Cl$_2$. The organic layer was dried and the solvent was removed in vacuo. The resulting crude solid was triturated with Et$_2$O, filtered and dried, yielding 1.16 g of the title product.

IR, $^1$H nmr spectra and mass spectra were consistent with the assigned structure.

Preparation 21

(±)-1-Benzyloxy-7-[(4-phenylpiperidin-1-yl)
carbonyl]-6,7,8,9-tetrahydro-5H-benzocyclohepten-
5-one 600 mg (0.00165 mol) of (±)-1-hydroxy-7-[(4-phenylpiperidin-1-yl)carbonyl]-6,7,8,9-tetrahydro-5H-benzocyclohepten-5-one were dissolved in 100 mL of abs. EtOH under a nitrogen atmosphere, then 228 mg (0.00165 mol) of anhydrous K$_2$CO$_3$ and a catalytic amount of KI were added, followed by 0.216 mL (0.0018 mol) of benzylbromide. The reaction mixture was stirred 3 h at room temperature, then 0.216 mL of benzylbromide were added and the stirring continued overnight. Further 0.216 mL of benzylbromide was added and the reaction stirred overnight. The solvent was then evaporated, the residue was taken up in water, brought to pH 1 with 1N HCl and extracted with AcOEt. The organic phase was dried and the solvent was removed in vacuo, the resulting crude product was purified by flash chromatography, eluting with a mixture Et$_2$O/Hexane 8:2 respectively, yielding 595 mg of the title compound.

IR, $^1$H nmr spectra and mass spectra were consistent with the assigned structure.

EXAMPLE 1

2,3-Dihydro-2-[(4-phenylpiperidin-1-yl)methyl]
indene hydrochloride 630 mg (2.06 mmol) of 2,3-dihydro-2-[(4-phenylpiperidin-1-yl)carbonyl]-1H-indene dissolved in 10 mL of dry THF were added dropwise to a suspension of 300 mg of LiAlH$_4$ in 40 mL of dry THF at room temperature. The reaction mixture was stirred 2 h, then it was quenched by sequential addition of 0.35 mL of water, 1 mL of 15% NaOH and 0.35 mL of water and stirred for 90 min. The resulting precipitate was filtered by suction and the filtrate was evaporated to dryness. The resulting residue was dissolved in THF, brought to acidic pH with Et$_2$O/HCl and the solvent was removed in vacuo. The resulting solid was triturated with hot acetone, filtered and dried, yielding 370 mg of the title compound. m.p.>240° C. IR (cm$^{-1}$)=2930, 2376, 1478. NMR (300 MHz, CDCl$_3$, δ ppm): 7.30–7.10 (m, 1H); 3.10–3.02 (m, 4H); 2.80–2.69 (m, 3H); 2.55–2.41 (m, 1H); 2.42 (d, 2H); 2.12–2.02 (m, 2H); 1.86–1.78 (m, 4H). MS (m/z): 292 (MH$^+$).

Compounds of formula I" and described in Table 2 were obtained following procedure described in Example 1.

TABLE 2

I''

![Structure showing pyrrolidine/piperidine ring with X, Y substituents and B-CH2-N linkage]

| Ex n° | Name | B | X | Y | m | n | m.p. (°C.) | IR (cm⁻¹) | NMR (300 MHz) δ ppm | MS (m/z) (MH⁺) |
|---|---|---|---|---|---|---|---|---|---|---|
| 2 | (±)-3-[(4-Phenylpiperidine-1-yl)methyl]-1-hydroxy-2H-3,4-dihydronaphthalene | [dihydronaphthalene with OH] | Ph | H | 2 | 1 | 107–108 | 3398, 2936, 1450 | (CDCl$_3$): 7.51(d, 1H); 7.32–7.17(m, 7H); 7.09(d, 1H); 5.00–4.50 (s br, 1H); 4.79(t, 1H); 3.11(dq, 1H); 2.98(dd, 1H); 2.90(dq, 1H); 2.59–2.44(m, 2H); 2.41–2.29(m, 3H); 2.23–2.01(m, 3H); 1.98–1.72(m, 5H). | 322 |
| 3 | (±)-2-[(4-Phenylpiperidin-1-yl)methyl]-1,2-3,4-tetrahydronaphthalene hydrochloride | [tetrahydronaphthalene] | Ph | H | 2 | 1 | 264–265 | 3026, 2928, 1492 | (CDCl$_3$): 12.40(s br, 1H); 7.32–7.05(m, 9H); 3.72(m, 2H); 3.15–2.67(m, 11H); 2.47(m, 1H); 2.31(m, 1H); 2.00(m, 2H); 1.74–1.61(m, 1H). | 306 |

EXAMPLE 4

(±)-3-[(4-Phenylpiperidin-1-yl)methyl]-1-oxo-2H-3,4-dihydronaphthalene hydrochloride 1.5 g of activated MnO$_2$ were added to a stirred solution of 1.2 g of (±)-3-[(4-phenylpiperidin-1-yl)methyl]-1-hydroxy-2H-3,4-dihydronaphthalene in 20 mL of AcOEt. The stirring was continued for 7 days, then the resulting mixture was filtered and the filtrate evaporated to dryness. The crude product was purified by column chromatography, eluting with a mixture hexane/AcOEt 9:1 respectively, yielding 0.7 g of free base which was dissolved in Et$_2$O, brought to acidic pH with Et$_2$O/HCl and evaporated to dryness The resulting solid was triturated with Et$_2$O, filtered and dried, yielding 0.65 g of the title compound. m.p. 261–262° C. IR (cm⁻¹)=3028, 2934, 1678. NMR: (300 MHz, CDCl$_3$, δ ppm): 8.03 (dd, 1H); 7.49 (dt, 1H); 7.33–7.18 (m, 7H); 3.12 (d, 1H); 3.03–2.92 (m, 2H); 2.86 (d, 1H); 2.75 (dd, 1H); 2.55–2.30 (m, 5H); 2.16–2.02 (m, 2H); 1.84–1.76 (m, 4H). MS (m/z): 320 (MH⁺)

Compounds of formula I'' and described in Table 3 were obtained following procedure described in Example 4.

TABLE 3

I''

![Structure showing pyrrolidine/piperidine ring with X, Y substituents and B-CH2-N linkage]

| Ex n° | Name | B | X | Y | m | n | m.p. (°C.) | IR (cm⁻¹) | NMR (300 MHz) δ ppm | MS (m/z) (MH⁺) | [α]$^{20}_D$ |
|---|---|---|---|---|---|---|---|---|---|---|---|
| 5 | (R)-(−)-3-[(4-Phenylpiperidin-1-yl)methyl]-1-oxo-2H-3,4-dihydronaphthalene hydrochloride | [oxo-dihydronaphthalene] | Ph | H | 2 | 1 | 259–260 | 3028, 2934, 1678 | (CDCl$_3$): 8.03(dd, 1H); 7.49(dt, 1H); 7.33–7.18(m, 7H); 3.12(d, 1H); 3.03–2.92(m, 2H); 2.86(d, 1H); 2.75(dd, 1H); 2.55–2.30(m, 5H); 2.16–2.02(m, 2H); 1.84–1.76(m, 4H). | 320 | −11.30 c = 0.5, MeOH |

TABLE 3-continued

I"

| Ex n° | Name | B | X | Y | m | n | m.p. (° C.) | IR (cm⁻¹) | NMR (300 MHz) δ ppm | MS (m/z) (MH⁺) | [α]²⁰_D |
|---|---|---|---|---|---|---|---|---|---|---|---|
| 6 | (S)-(+)-3-[(4-Phenylpiperidin-1-yl)methyl]-1-oxo-2H-3,4-dihydronaphthalene hydrochloride | (1-oxo-tetralin structure) | Ph | H | 2 | 1 | 257–258 | 3030, 2930, 1678 | (CDCl₃); 8.03(dd, 1H); 7.49(dt, 1H); 7.33–7.18(m, 7H); 3.12(d, 1H); 3.03–2.92(m, 2H); 2.86(d, 1H); 2.75(dd, 1H); 2.55–2.30(m, 5H); 2.16–2.02(m, 2H); 1.84–1.76(m, 4H). | 320 | +11.74 c = 0.5, MeOH |
| 7 | (±)-1,2-Dihydro-2-[(4-phenylpiperidin-1-yl)methyl]phenanthren-4-(3H)-one hydrochloride | (phenanthrenone structure) | Ph | H | 2 | 1 | — | — | — | — | — |

EXAMPLE 8

(±)-2-[(4-Phenylpiperidin-1-yl)methyl]-1,2-dihydronaphthalene hydrochloride 0.5 g of (±)-3-[(4-phenylpiperidin-1-yl)methyl]-1-hydroxy-2H-3,4-dihydronaphthalene were dehydrated with Et₂O/HCl at room temperature, yielding 0.3 g of the title compound. m.p.=239–240° C.; IR (cm⁻¹)=2932, 2604, 1494. NMR: (300 MHz, DMSO, 353K, as a base, δ ppm): 7.30–7.02 (m, 9H); 6.46 (d, 1H); 6.00 (dd, 1H); 2.89 (m, 2H); 2.65 (m, 2H); 2.40 (m, 2H); 2.10 (m, 4H); 1.80–1.60 (m, 4H). MS (m/z): 304 (MH⁺).

EXAMPLE 9

(±)-cis-7-[(4-Phenylpiperidin-1-yl)methyl]-6,7,8,9-tetrahydro-5H-benzocyclohepten-5-ol 0.15 g (3.8 mmol) of LiAlH₄ were added to a solution of 0.33 g (0.95 mmol) of (±)-7-[(4-phenylpiperidin-1-yl)carbonyl]-6,7,8,9-tetrahydro-5H-benzocyclohepten-5-one in 15 mL of dry Et₂O at 0° C. and the resulting mixture was heated to reflux overnight. After cooling, the reaction was quenched by the careful addition of 0.5 mL of 2 N NaOH, the suspension was stirred 10 min and then filtered by suction on a Celite pad washing with Et₂O. The solvent was removed in vacuo, yielding 0.25 g of the title compound. m.p.=48–50° C.

Compounds of formula I" and described in Table 4 were obtained following procedure described in Example 9.

TABLE 4

I"

| Ex n° | Name | B | X | Y | m | n | m.p. (° C.) |
|---|---|---|---|---|---|---|---|
| 10 | (±)-1-Methoxy-7-[(4-phenylpiperidin-1-yl)methyl]-6,7,8,9-tetrahydro-5H-benzocyclohepten-5-ol | (5-hydroxy-1-methoxy-benzocycloheptene structure) | Ph | H | 2 | 1 | 46–48 |

TABLE 4-continued

|  |  |  |  |  |  |  |  |
|---|---|---|---|---|---|---|---|
| Ex n° | Name | B | X | Y | m | n | m.p. (° C.) |
| 11 | (±)-3-Methoxy-7-[(4-phenylpiperidin-1-yl)methyl]-6,7,8,9-tetrahydro-5H-benzocyclohepten-5-ol | (structure: MeO, HO-substituted benzocycloheptene) | Ph | H | 2 | 1 | 45–48 |

EXAMPLE 12

(±)-7-[(4-Phenylpiperidin-1-yl)methyl]-6,7,8,9-tetrahydro-5H-benzocyclohepten-5-one hydrochloride 0.17 mL of the Jones reagent (prepared by mixing 2.67 g of $CrO_3$ and 2.3 mL of conc. $H_2SO_4$ and adding water up to a final volume of 10 mL) were added to a solution of 0.2 g (0.6 mmol) of (±)-7-[(4-phenylpiperidin-1-yl)methyl]-6,7,8,9-tetrahydro-5H-benzocyclohepten-5-ol in 13 mL of acetone. The solution was stirred at room temperature for 1 h, then the solvent was removed in vacuo, the residue was taken up in water, brought to basic pH with 10% NaOH and extracted with $CH_2Cl_2$. The organic phase was dried and the solvent was removed in vacuo, obtaining 0.15 g of an oil which was dissolved in $Et_2O$ and brought to acidic pH with $Et_2O$/HCl. The resulting white solid was triturated with $Et_2O$, filtered and dried, yielding 0.1 g of the title compound. m.p.=220° C. (dec.).

Compounds of formula I″ and described in Table 5 were obtained following procedure described in Example 12.

TABLE 5

|  |  |  |  |  |  |  |  |
|---|---|---|---|---|---|---|---|
| Ex. n° | Name | B | X | Y | m | n | m.p. (° C.) |
| 13 | (±)-1-Methoxy-7-[(4-phenylpiperidin-1-yl)methyl]-6,7,8,9-tetrahydro-5H-benzocyclohepten-5-one hydrochloride | (structure: benzocycloheptenone with OMe) | Ph | H | 2 | 1 | 140–143 |
| 14 | (±)-3-Methoxy-7-[(4-phenylpiperidin-1-yl)methyl]-6,7,8,9-tetrahydro-5H-benzocyclohepten-5-one hydrochloride | (structure: MeO-benzocycloheptenone) | Ph | H | 2 | 1 | 185–188 |

EXAMPLE 15

(±)-cis-5-Methoxy-7-[(4-phenylpiperidin-1-yl)methyl]-6,7,8,9-tetrahydro-5H-benzocycloheptene hydrochloride A solution of 0.1 g (0.3 mmol) of (±)-7-[(4-phenylpiperidin-1-yl)methyl]-6,7,8,9-tetrahydro-5H-benzocyclohepten-5-ol in 2 mL of MeOH and 0.05 mL of conc. $H_2SO_4$ was refluxed overnight. After cooling, the solvent was removed in vacuo, the residue was taken up in 10% NaOH and extracted with AcOEt. The organic phase was washed with water, dried and the solvent was removed in vacuo. The crude product was purified by flash chromatography, eluting with a mixture $CH_2Cl_2$/MeOH 95:5 respectively, obtaining the cis diastereoisomer as the faster eluting compound. The compound was dissolved in $Et_2O$ and brought to acidic pH with $Et_2O$/HCl. The resulting white solid was triturated with $Et_2O$, filtered and dried, yielding 0.03 g of the title compound. m.p.=213–215° C. NMR: (300 MHz, $CDCl_3$, as a base, δ ppm): 7.47 (d, 1H); 7.30–7.10 (m, 8H); 4.38 (d, 1H); 3.49 (s, 3H); 2.98 (m, 2H); 2.84–2.70 (m, 2H); 2.53–2.41 (m, 1H); 2.30 (dd, 1H); 2.20–1.95 (m, 6H); 1.85–1.73 (m, 4H); 1.20 (dd, 1H); 1.00–1.89 (m, 1H).

EXAMPLE 16

(±)-trans-5-Methoxy-7-[(4-phenylpiperidin-1-yl)methyl]-6,7,8,9-tetrahydro-5H-benzocycloheptene hydrochloride The chromatography of the preceding example was continued, obtaining the trans diastereoisomer as the slower eluting compound. The compound was dissolved in $Et_2O$ and brought to acidic pH with $Et_2O$/HCl. The resulting white solid was triturated with $Et_2O$, filtered and dried, yielding 0.02 g of the title compound. (m.p.=220–222° C.). NMR: (300 MHz, $CDCl_3$, δ ppm): 7.30–7.10 (m, 9H); 4.35 (d, 1H); 3.20 (s, 3H); 3.20 (d, 1H); 3.01 (m, 2H); 2.65 (m, 1H); 2.55–2.30 (m, 3H); 2.20–1.95 (m, 5H); 1.80 (m, 4H); 1.31 (dt, 1H); 1.01 (dt, 1H).

EXAMPLE 17

1-(2,3-Dihydro-1H-inden-2-yl)4-phenylpiperidine hydrochloride 190 mg (3 mmol) of $NaCNBH_3$ were added portionwise at room temperature to a stirred solution of 200 mg (1.5 mmol) of 2-indanone, 490 mg (3 mmol) of 4-phenylpiperidine and 0.35 mL (6 mmol) of glacial acetic acid in 20 mL of MeOH. After stirring overnight, the solvent was removed in vacuo and the residue was taken up, in water, brought to basic pH with 10% NaOH and extracted with AcOEt. The organic phase was dried and the solvent removed in vacuo; the resulting crude product was purified by flash chromatography, eluting with a mixture n-hexane/AcOEt 8:2 respectively. The compound was dissolved in $Et_2O$ and brought to acidic pH with $Et_2O$/HCl. The solvent was removed in vacuo and the product was crystallised from $(i-Pr)_2O$, yielding 190 mg of the title compound. m.p.>250° C. IR (cm−1)=2927, 2444, 1469. NMR: (300 MHz, $CDCl_3$, δ ppm): 7.30–7.10 (m, 9H); 3.29–3.09 (m, 5H); 2.96 (dd, 2H); 2.59–2.49 (m, 1H); 2.21–2.11 (m, 2H); 1.90–1.80 (m, 4H). MS (m/z): 278 (MH+).

EXAMPLE 18

N-(6,7,8,9-Tetrahydro-5H-benzocyclohepten-7-yl)-4-phenylpiperidine hydrochloride The title compound was obtained according to the method described in Example 17, starting from 3-benzosuberone (prepared as described in Ewing, J. Org. Chem., 40, 2965, 1975). m.p.>250° C. IR (KBr, cm−1): 2940, 2466, 1455. NMR (300 MHz, $CDCl_3$, δ ppm): 7.32–7.19 (m, 9H); 2.93–2.78 (m, 7H); 2.48–2.39 (m, 3H); 2.20–2.10 (m, 2H); 1.88–1.68 (m, 4H); 1.45 (dt, 2H). MS (m/z): 306 (MH+).

EXAMPLE 19

(±)-cis-1-Methyl-7-[[4-(2-methylphenyl)piperidin-1-yl]methyl]-6,7,8,9-tetrahydro-5H-benzocyclohepten-5-ol hydrochloride 729 mg (1.94 mmol) of (±)-1-methyl-7-[[4-(2-methylphenyl)piperidin-1-yl]carbonyl]-6,7,8,9-tetrahydro-5H-benzocyclohepten-5-one dissolved in 20 mL of dry THF were added dropwise, at 0° C. and under a nitrogen atmosphere, to a suspension of 300 mg of $LiAlH_4$ in 15 mL of dry THF. The reaction mixture was allowed to warm to room temperature then heated at 60° C. for 3 h. After cooling, it was quenched by adding, at 0° C., 0.3 mL $H_2O$, 1 mL 15% NaOH and 0.3 mL $H_2O$. After stirring for 1 h, the resulting precipitate was filtered by suction and the filtrate was evaporated to dryness. The resulting residue was purified by flash chromatography, eluting with a mixture $CH_2Cl_2$/MeOH/conc. $NH_4OH$ 100:3:0.3 respectively, yielding 319 mg of compound, which was dissolved in $Et_2O$, brought to acidic pH with $Et_2O$/HCl and the solvent was removed in vacuo. The resulting solid was triturated with hot acetone, filtered and dried, yielding 290 mg of the title compound. m.p.>250° C. IR (KBr, cm−1)=3248, 2924, 1463. NMR: (300 MHz, $CDCl_3$, δ ppm): 7.43 (d, 1H); 7.25 (d, 1H); 7.21–7.05 (m, 5H); 5.02 (d, 1H); 3.03 (dd, 1H); 3.00 (m, 2H); 2.75–2.64 (m, 1H); 2.47 (dd, 1H); 2.33 (s, 6H); 2.25 (d, 1H); 2.19–2.00 (m, 4H); 2.13 (s, 2H); 1.88–1.70 (m, 4H); 1.35 (m, 1H); 0.89 (m, 1H). MS (m/z): 363 (M+.); 188;

Compounds of formula I″ and described in Table 6 were obtained following procedure described in Example 19.

TABLE 6

I″

| Ex n° | Name | B |
|---|---|---|
| 20 | (±)-1,3-dimethyl-7-[(4-phenylpiperidin-1-yl)methyl]-6,7,8,9-tetrahydro-5H-benzocyclohepten-5-ol | |
| 21 | (±)-cis-7-[[4-(2-methoxyphenyl)piperidin-1-yl]methyl]-6,7,8,9-tetrahydro-5H-benzocyclohepten-5-ol | |

TABLE 6-continued

| | | I'' |
|---|---|---|
| 22 | (±)-cis-3-chloro-7-[(4-phenylpiperidin-1-yl)methyl]-6,7,8,9-tetrahydro-5H-benzocyclohepten-5-ol | |
| 23 | (±)-1-chloro-7-[(4-phenylpiperidin-1-yl)methyl]-6,7,8,9-tetrahydro-5H-benzocyclohepten-5-ol | |
| 24 | (±)-7-[[4-(2-hydroxyphenyl)piperidin-1-yl]methyl]-6,7,8,9-tetrahydro-5H-benzocyclohepten-5-ol hydrochloride | |
| 25 | (±)-cis-7-[[4-(3-fluorophenyl)piperidin-1-yl]methyl]-6,7,8,9-tetrahydro-5H-benzocyclohepten-5-ol hydrochloride | |
| 26 | (±)-cis-7-[[4-(2-methylphenyl)piperidin-1-yl]methyl]-6,7,8,9-tetrahydro-5H-benzocyclohepten-5-ol hydrochloride | |
| 27 | (±)-cis-1-methyl-7-[(4-phenylpiperidin-1-yl)methyl]-6,7,8,9-tetrahydro-5H-benzocyclohepten-5-ol | |
| 28 | (±)-cis-7-[[4-(4-benzyloxyphenyl)piperidin-1-yl]methyl]-6,7,8,9-tetrahydro-5H-benzocyclohepten-5-ol hydrochloride | |
| 29 | (±)-cis-7-[[4-(3-bromophenyl)piperidin-1-yl]methyl]-6,7,8,9-tetrahydro-5H-benzocyclohepten-5-ol hydrochloride | |
| 30 | (±)-1-fluoro-7-[(4-phenylpiperidin-1-yl)methyl]-6,7,8,9-tetrahydro-5H-benzocyclohepten-5-ol hydrochloride | |
| 31 | (±)-7-[[4-(4-fluorophenyl)piperidin-1-yl]methyl]-6,7,8,9-tetrahydro-5H-benzocyclohepten-5-ol hydrochloride | |
| 32 | (±)-7-[[4-(3,5-dimethoxyphenyl)piperidin-1-yl]methyl]-6,7,8,9-tetrahydro-5H-benzocyclohepten-5-ol hydrochloride | |
| 33 | (±)-cis-1-phenyl-7-[(4-phenylpiperidin-1-yl)methyl]-6,7,8,9-tetrahydro-5H-benzocyclohepten-5-ol hydrochloride | |
| 34 | (±)-7-[[4-(2-chlorophenyl)piperidin-1-yl]methyl]-6,7,8,9-tetrahydro-5H-benzocyclohepten-5-ol hydrochloride | |
| 35 | (±)-cis-1-bromo-7-[(4-phenylpiperidin-1-yl)methyl]-6,7,8,9-tetrahydro-5H-benzocyclohepten-5-ol hydrochloride | |

TABLE 6-continued

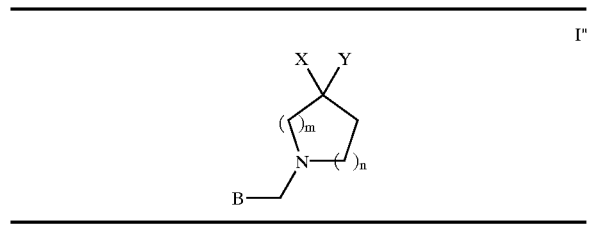

| | | |
|---|---|---|
| 36 | (±)-1-benzyloxy-7-[(4-phenylpiperidin-1-yl)methyl]-6,7,8,9-tetrahydro-5H-benzocyclohepten-5-ol hydrochloride | 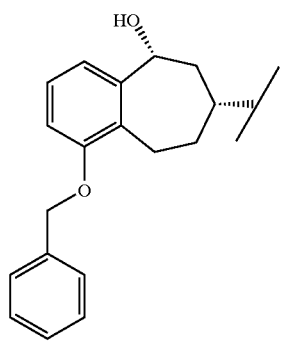 |
| 37 | (±)-cis-1-methyl-7-[[4-(3-fluorophenyl)piperidin-1-yl]methyl]-6,7,8,9-tetrahydro-5H-benzocyclohepten-5-ol hydrochloride | 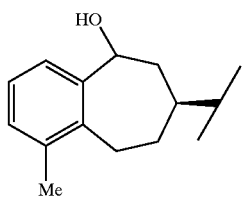 |
| 38 | (±)-cis-1-methoxy-7-[[4-(2-methylphenyl)piperidin-1-yl]methyl]-6,7,8,9-tetrahydro-5H-benzocyclohepten-5-ol | 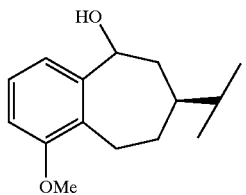 |
| 39 | (±)-trans-1-methoxy-7-[[4-(2-methylphenyl)piperidin-1-yl]methyl]-6,7,8,9-tetrahydro-5H-benzocyclohepten-5-ol | 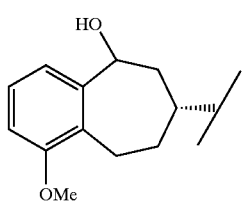 |
| 40 | (±)-cis-1-methoxy-7-[[4-(3-fluorophenyl)piperidin-1-yl]methyl]-6,7,8,9-tetrahydro-5H-benzocyclohepten-5-ol | 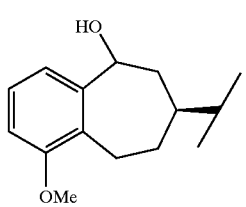 |
| 41 | (±)-trans-1-methoxy-7-[[4-(3-fluorophenyl)piperidin-1-yl]methyl]-6,7,8,9-tetrahydro-5H-benzocyclohepten-5-ol | 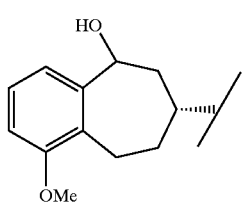 |

TABLE 6-continued

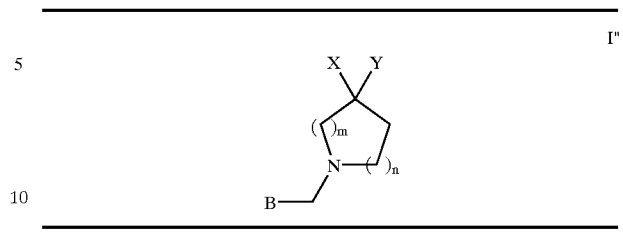

| | | |
|---|---|---|
| 42 | (±)-cis-1-hydroxy-7-[(4-phenylpiperidin-1-yl)methyl]-6,7,8,9-tetrahydro-5H-benzocyclohepten-5-ol hydrochloride | 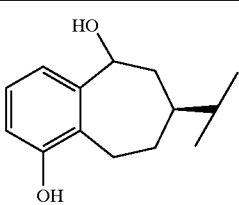 |
| 43 | (±)-4-methoxy-7-[(4-phenylpiperidin-1-yl)methyl]-6,7,8,9-tetrahydro-5H-benzocyclohepten-5-ol hydrochloride | 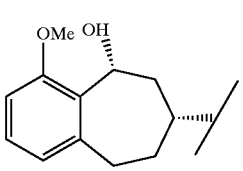 |

| Ex n° | X | Y | m | n | m.p. (°C.) |
|---|---|---|---|---|---|
| 20 | Ph | H | 2 | 1 | 52–55 |
| 21 | (2-OMe)Ph | H | 2 | 1 | 72–74 |
| 22 | Ph | H | 2 | 1 | — |
| 23 | Ph | H | 2 | 1 | — |
| 24 | (2-OH)Ph | H | 2 | 1 | 158–160 |
| 25 | (3-F)Ph | H | 2 | 1 | 238–240 |
| 26 | (2-Me)Ph | H | 2 | 1 | >250 |
| 27 | Ph | H | 2 | 1 | 52–55 |
| 28 | (4-OBn)Ph | H | 2 | 1 | 225–228 |
| 29 | (3-Br)Ph | H | 2 | 1 | >250 |
| 30 | Ph | H | 2 | 1 | 218–220 |
| 31 | (4-F)Ph | H | 2 | 1 | 227–229 |
| 32 | (3,5-di-OMe)Ph | H | 2 | 1 | 223–225 |
| 33 | Ph | H | 2 | 1 | 245–246 |
| 34 | (2-Cl)Ph | H | 2 | 1 | 239–240 |
| 35 | Ph | H | 2 | 1 | 220–224 |
| 36 | Ph | H | 2 | 1 | 198–202 |
| 37 | (3-F)Ph | H | 2 | 1 | 241–243 |
| 38 | (2-Me)Ph | H | 2 | 1 | — |
| 39 | (2-Me)Ph | H | 2 | 1 | — |
| 40 | (3-F)Ph | H | 2 | 1 | — |
| 41 | (3-F)Ph | H | 2 | 1 | — |
| 42 | Ph | H | 2 | 1 | 190–193 |
| 43 | Ph | H | 2 | 1 | 176–189 |

TABLE 6-continued

I"

[Structure: pyrrolidine-like ring with X, Y substituents, (  )m and (  )n, N-CH2-B]

| Ex n° | Ir (cm⁻¹) | NMR (δ ppm) | MS (m/z) |
|---|---|---|---|
| 20 | IR and ¹H nmr spectra were consistent with the assigned structure. | | |
| 21 | IR, ¹H nmr spectra and mass spectra were consistent with the assigned structure | | |
| 22 | IR, ¹H nmr spectra and mass spectra were consistent with the assigned structure. | | |
| 23 | (KBr); 3290, 1580. 1455. | (200 MHz, CDCl3): 7.5(d, 1H); 7.4–7.1(m, 7H); 5.0(d, 1H); 3.6–3.4(m, 1H); 3.1–2.9(m, 2H); 2.8–2.6(m, 3H); 2.3–1.9(m, 7H); 1.9–1.7(m, 5H). | — |
| 24 | IR, ¹H nmr spectra were consistent with the asisgned structure. | | |
| 25 | (KBr); 3295, 2925, 1588. | (300 MHz, CDCl₃, +D₂O + Na₂CO₃, 333 K): 7.49(d, 1H); 7.19–7.09(m, 2H); 7.02–6.89(m, 3H); 6.81(d, 1H); 6.75(dd, 1H); 4.82(d, 1H); 2.89(m, 2H); 2.75–2.60(m, 2H); 2.48(m, 2H); 2.48–2.34(m, 1H); 2.15–1.90(m, 6H); 1.75–1.61(m, 4H); 1.20(dt, 1H); 0.90–0.80(m, 1H). | 353 (M+.); 192; 149 |
| 26 | (KBr); 3293; 2926, 1454. | (300 MHz, CDCl3): 7.59(d, 1H); 7.25–7.04(m, 7H); 4.99(d, 1H); 3.00(dd, 2H); 2.89–2.65(m, 3H); 2.32(s, 3H); 2.27(d, 1H); 2.18–2.01(m, 6H); 1.88–1.70(m, 4H); 1.35(dt, 1H); 0,99(dt, 1H). | 349 (M+.); 188 |
| 27 | (KBr); 3293; 1540. 1454. | (200 MHz, CDCl3): 7.5–7.0(m, 8H); 5.05(d, 1H); 3.2–2.9(m, 2H); 2.6–2.3(m, 2H; s, 3H); 2.3–1.9 (m, 8H); 1.9–1.5(m, 7H). | — |
| 28 | IR, ¹H nmr spectra and mass spectra were consistent with the assigned structure. | | |
| 29 | IR, ¹H nmr spectra were consistent with the assigned structure. | | |
| 30 | (KBr); 3338; 2927, 1463. | (300 MHz, CDCl3, 343K): 7.36(d, 1H); 7.31–7.14(m, 6H); 6.91(dd, 1H); 4.96(d, 1H); 3.39 (ddd, 1H); 2.99(m, 2H); 2.56–2.46(m, 1H); 2.40–2.21(m, 2H); 2.20–2.05(m, 6H); 1.88–1.79(m, 4H); 1.39(dt, 1H); 0.98(dt, 1H). | 353 (M+.); 174; |
| 31 | (KBr); 3269; 2930, 1511. | (300 MHz, CDCl3): 7.59(d, 1H); 7.30–7.12(m, 4H); 7.10(dd, 1H); 6.99(dd, 2H); 4.98(d, 1H); 2.99(m, 2H); 2.88–2.70(m, 2H); 2.52–2.42(m, 1H); 2.29–1.99(m, 7H); 1.81–1.70(m, 4H); 1.38 (dt, 1H); 0.99(dt, 1H). | 353 (M+.); 192 |
| 32 | IR, ¹H nmr spectra were consistent with the assigned structure. | | |
| 33 | IR, ¹H nmr spectra were consistent with the assigned structure. | | |
| 34 | (KBr); 3291; 2928, 1441. | (300 MHz, CDCl3): 7.58(d, 1H); 7.35–7.09(m, 7H); 4.98(d, 1H); 3.07–2.85(m, 3H); 2.89–2.70 (m, 2H); 2.30–2.03(m, 6H); 1.88–1.60(m, 5H); 1.38(dt, 1H); 0,99(dt, 1H). | 369 (M+.); 208; 174 |
| 35 | (KBr); 3344; 2937, 1445. | (300 MHz, CDCl3): 7.54(d, 1H); 7.46(d, 1H); 7.32–7.17(m, 5H); 7.08(dd, 1H); 5.01(d, 1H); 3.55(dd, 1H); 2.98(m, 2H); 2.59(dd, 1H); 2.55–2.43(m, 1H); 2.25(d, 1H); 2.13(s, 2H); 2.13–2.00(m, 4H); 1.92–1.68(m, 4H); 1.32(m, 1H), 0,90(m, 1H). | 413 (M+.); 174 |
| 36 | IR, ¹H nmr spectra and mass spectra were consistent with the assigned structure. | | |
| 37 | (KBr); 3270; 2930, 1440. | (300 MHz, CDCl3): 7.42(d, 1H); 7.28–7.21(m, 1H); 7.14(dd, 1H); 7.06(d, 1H); 7.00(d, 1H); 6.96–6.84(m, 2H); 5.40(d, 1H); 3.12(dd, 1H); 2.97(m, 2H); 2.54–2.41(m, 2H); 2.31(s, 3H); 2.22(d, 1H); 2.19–2.00(m, 4H); 2.12(s, 2H); 1.82–1.70(m, 4H); 1.31(m, 1H); 0.89(m, 1H). | 367 (M+.); 192 |
| 38 | (KBr); 3300; 1540, 1463. | (200 MHz, CDCl3): 7.3–7.1(m, 6H); 6.8(m, 1H); 5.0(d, 1H); 3.8(s, 3H); 3.5(m, 1H); 3.1–2.9(m, 2H); 2.9–2.6(m, 1H); 2.35(s, 3H); 2.3–1.9(m, 9H); 1.9–1.7(m, 4H); 1.35–1.2(m, 1H); 0.9(m, 1H). | — |
| 39 | IR and ¹H nmr spectra were consistent with the assigned structure. | | |
| 40 | IR and ¹H nmr spectra were consistent with the assigned structure. | | |
| 41 | (KBr); 3295; 1580, 1455. | (200 MHz, CDCl3): 7.3–6.8(m, 7H); 5.0(d, 1H); 3.8(s, 3H); 3.2(m, 1H); 2.5(m, 1H); 2.4–2.1(m, 4H); 2.1–1.6(m, 10H); 0.9(m, 1H). | — |
| 42 | IR and ¹H nmr spectra were consistent with the assigned structure. | | |
| 43 | IR and ¹H nmr spectra were consistent with the assigned structure. | | |

Compounds of formula I" and described in Table 7 were obtained following procedure described in Example 12.

TABLE 7

I"

[Structure: pyrrolidine-like ring with X, Y substituents, (  )m and (  )n, N-CH2-B]

| Ex n° | Name | B |
|---|---|---|
| 44 | (±)-1,3-dimethyl-7-[(4-phenylpiperidin-1-yl)methyl]-6,7,8,9-tetrahydro-5H-benzocyclohepten-5-one hydrochloride | [structure] |
| 45 | (±)-7-[[4-(2-methoxyphenyl)piperidin-1-yl]methyl]-6,7,8,9-tetrahydro-5H-benzocyclohepten-5-one hydrochloride | [structure] |
| 46 | (±)-3-chloro-7-[(4-phenylpiperidin-1-yl)methyl]-6,7,8,9-tetrahydro-5H-benzocyclohepten-5-one hydrochloride | [structure] |
| 47 | (±)-1-chloro-7-[(4-phenylpiperidin-1-yl)methyl]-6,7,8,9-tetrahydro-5H-benzocyclohepten-5-one hydrochloride | [structure] |

TABLE 7-continued

[Structure: bicyclic ketone with X, Y substituents, connected via CH₂ to N of piperidine-type ring with (CH₂)m and (CH₂)n, labeled B—]

| Ex n° | Compound |
|---|---|
| 48 | (±)-7-[[4-(2-hydroxyphenyl)piperidin-1-yl]methyl]-6,7,8,9-tetrahydro-5H-benzocyclohepten-5-one hydrochloride |
| 49 | (±)-1-methyl-7-[(4-phenylpiperidin-1-yl)methyl]-6,7,8,9-tetrahydro-5H-benzocyclohepten-5-one hydrochloride |
| 50 | (±)-7-[[4-(2-methylphenyl)piperidin-1-yl]methyl-6,7,8,9-tetrahydro-5H-benzocyclohepten-5-one hydrochloride |

| Ex n° | X | Y | m | n | m.p. (° C.) |
|---|---|---|---|---|---|
| 44 | Ph | H | 2 | 1 | 222–225 |
| 45 | (2-OMe)Ph | H | 2 | 1 | 232–234 |
| 46 | Ph | H | 2 | 1 | 180–185 |
| 47 | Ph | H | 2 | 1 | — |
| 48 | (2-OH)Ph | H | 2 | 1 | 216–218 |
| 49 | Ph | H | 2 | 1 | 205–210 |
| 50 | (2-Me)Ph | H | 2 | 1 | 202–205 |

| Ex n° | IR (cm⁻¹) | NMR (δ ppm) | MS (m/z) |
|---|---|---|---|
| 44 | IR and ¹H nmr spectra were consistent with the assigned structure. | | |
| 45 | IR, and ¹H nmr spectra and mass spectra were consistent with the assigned structure. | | |
| 46 | IR and ¹H nmr spectra were consistent with the assigned structure. | | |
| 47 | IR and ¹H nmr spectra were consistent with the assigned structure. | | |
| 48 | IR, and ¹H nmr spectra were consistent with the assigned structure. | | |
| 49 | (neat, free base): 2900; 1670; 1450. | (200 MHz, CDCl₃): 7.5(d, 1H); 7.4–7.1(m, 7H); 3.1–2.8(m, 5H); 2.65–2.5(m, 2H); 2.4(s, 3H); 2.3–2.25(m, 2H); 2.2–1.9(m, 4H); 1.9–1.7(m, 4H); 1.7–1.5(m, 1H). | — |
| 50 | IR, and ¹H nmr spectra were consistent with the assigned structure. | | |

EXAMPLE 51

(±)-7-[(4-phenylpiperidin-1-yl)methyl]-6,7-dihydro-5H-benzocycloheptene hydrochloride 0.2 g (0.6 mmol) of (±)-7-[(4-phenylpiperidin-1-yl)methyl]-6,7,8,9-tetrahydro-5H-benzocyclohepten-5-ol were dissolved in 5 mL of 1,4-dioxane and 16 mL of 37% HCl and heated to reflux for 2 h. The reaction mixture was then basified with NaOH and extracted with $CH_2Cl_2$. The organic phase was dried and the solvent was removed in vacuo. The resulting crude product was purified by chromatography, eluting with a mixture $CH_2Cl_2$/MeOH 100:2 respectively; The compound was dissolved in $Et_2O$ and brought to acidic pH with $Et_2O$/HCl. The resulting white solid was triturated with $Et_2O$, filtered and dried, yielding 0.02 g of the title compound. m.p.=268–270° C.

IR, ¹H nmr spectra and mass spectra were consistent with the assigned structure.

EXAMPLE 52

7-[(4-phenylpiperidin-1-yl)methyl]-6,7,8,9-tetrahydro-5H-benzocycloheptene hydrochloride 0.2 g of (±)-7-[(4-phenylpiperidin-1-yl)methyl]-6,7-dihydro-5H-benzocycloheptene were dissolved in 20 mL of MeOH, added to a suspension of 100 mg of 10% Pd—C in 5 mL of MeOH and hydrogenated at 50 psi for 6 h. The catalyst was filtered off, the solvent was removed in vacuo and the resulting crude product was purified by chromatography, eluting with a mixture $CH_2Cl_2$/MeOH 100:2 respectively. The compound was dissolved in $Et_2O$ and brought to acidic pH with $Et_2O$/HCl. The resulting white solid was triturated with $Et_2O$, filtered and dried, yielding 0.04 g of the title compound. m.p.>250° C.

IR, ¹H nmr spectra and mass spectra were consistent with the assigned structure.

EXAMPLE 53

7-[[4-(2-Methylphenyl)piperidin-1-yl]methyl]-6,7,8,9-tetrahydro-5H-benzocycloheptene hydrochloride The title compound was obtained as described in Examples 51 and 52 starting from (±)-7-[[4-(2-methylphenyl)piperidin-1-yl]methyl]-6,7,8,9-tetrahydro-5H-benzocyclohepten-5-ol. m.p. 245° C. (dec.).

IR, ¹H nmr spectra and mass spectra were consistent with the assigned structure.

EXAMPLE 54

(±)-cis-5-Allyloxy-7-[(4-phenylpiperidin-1-yl)methyl]-6,7,8,9-tetrahydro-5H-benzocycloheptene hydrochloride 0.2 g (0.596 mmol) of (±)-cis-7-[(4-phenylpiperdin-1-yl)methyl]-6,7,8,9-tetrahydro-5H-benzocyclohepten-5-ol dissolved in 5 ML THF were added dropwise to a suspension of 0.029 g (0.715 mmol) of NaH (60% dispersion in mineral oil) in 10 mL THF. After 30 min at room temperature, 0.12 mL of allyl bromide were added and the reaction mixture was refluxed 8 h. After cooling, the reaction mixture was quenched by addition of MeOH and the solvent was removed in vacuo. The residue was taken up in 1 N NaOH and extracted with $CH_2Cl_2$; the organic phase was dried and the solvent was removed in vacuo. The resulting crude product was purified by chromatography, eluting with a mixture $CH_2Cl_2$/MeOH 100:2 respectively, yielding an oil which was dissolved in $Et_2O$; the solution was brought to acidic pH with $Et_2O$/HCl and the solvent was removed in vacuo. The resulting solid was triturated with $Et_2O$, yielding 65 mg of the title product. m.p. 126–128° C.

IR, ¹H nmr spectra and mass spectra were consistent with the assigned structure.

EXAMPLE 55

(±)-trans-7-[(4-phenylpiperidin-1-yl)methyl]-6,7,8,9-tetrahydro-5H-benzocyclohepten-5-ol hydrochloride 0.7 g (2.1 mmol) of (±)-7-[(4-phenylpiperidin-1-yl)methyl]-6,7,8,9-tetrahydro-5H-benzocyclohepten-5-one were dissolved in 40 mL of MeOH and 0.35 g of $NaBH_4$ were added portionwise. The reaction mixture was stirred 2 h at room temperature, the MeOH removed in vacuo, then the residue was taken up in 1N NaOH and extracted with $CH_2Cl_2$. The organic phase was dried and the solvent was removed in vacuo. The crude product was purified by chromatography, eluting with $CH_2Cl_2$ and then with a mixture $CH_2Cl_2$/MeOH 100:3 respectively, yielding 100 mg of trans isomer which was dissolved in a mixture $CH_2Cl_2$/$Et_2O$: The solution was brought to acidic pH with $Et_2O$/HCl and the solvent was removed in vacuo. The resulting solid was triturated with hot acetone, filtered and dried, yielding 90 mg of the title compound. m.p.>250° C.

IR, $^1H$ nmr spectra and mass spectra were consistent with the assigned structure.

EXAMPLE 56

(±)-cis-1-Methoxy-7-[(4-phenylpiperidin-1-yl)methyl]-6,7,8,9-tetrahydro-5H-benzocyclohepten-5-ol hydrochloride The diastereoisomeric mixture of Example 10 (150 mg) was chromatographed on silica gel by gradient elution starting from $CH_2Cl_2$ up to a mixture $CH_2Cl_2$/MeOH 100:3 respectively, to yield the cis diastereoisomer as the faster eluting compound. The compound was dissolved in $Et_2O$, the solution was brought to acidic pH with $Et_2O$/HCl and the solvent was removed in vacuo. The resulting solid was triturated with hot acetone, filtered and dried, yielding 100 mg of the title compound. m.p. 229–231° C.

NMR (free base, 400 MHz, $C_6D_6$, δ ppm): 7.49 (d, 1H); 7.24–7.02 (m, 6H); 6.60 (d, 1H); 4.75 (d, 1H); 3.79 (ddd, 1H); 3.41 (s, 3H); 2.75 (m, 2H); 2.34 (tt, 1H); 2.20 (m, 2H); 2.02 (m, 1H); 1.93–1.63 (m, 9H); 1.29 (dt, 1H); 0.84 (q br, 1H). MS (m/z): 366 (MH+); 348.

EXAMPLE 57

(±)-trans-1-Methoxy-7-[(4-phenylpiperidin-1-yl)methyl]-6,7,8,9-tetrahydro-5H-benzocyclohepten-5-ol hydrochloride The chromatography of the preceding example was continued, obtaining the trans diastereoisomer as the slower eluting compound. The compound was dissolved in $Et_2O$, the solution was brought to acidic pH with $Et_2O$/HCl and the solvent was removed in vacuo. The resulting solid was triturated with hot acetone, filtered and dried, yielding 40 mg of the title compound. m.p.>250° C.

NMR (free base, 400 MHz, $C_6D_6$, δ ppm): 7.21–7.03 (m, 6H); 6.88 (d, 1H); 6.60 (d, 1H); 4.79 (dd, 1H); 3.40 (m, 1H); 3.38 (s, 3H); 3.22 (ddd, 1H); 2.82 (m, 2H); 2.38 (m, 1H); 2.30 (m, 2H); 2.11 (m, 1H); 2.07 (d, 2H); 191–1.62 (m, 6H); 1.41 (ddd, 1H); 1.18 (dt, 1H). MS (m/z): 366 (MH+).

Racemic (±)-1-methoxy-7-[(4-phenylpiperidin-1-yl)methyl]-6,7,8,9-tetrahydro-5H-benzocyclohepten-5-one (compound of Example 13) was separated by preparative HPLC on chiral stationary phase (Daicel Chiracel OD, elution with 90:10:0.1 Hexane:Ethanol:Diethylamine, 12 mL/min), obtaining:

EXAMPLE 58

(+)-1-Methoxy-7-[(4-phenylpiperidin-1-yl)methyl]-6,7,8,9-tetrahydro-5H-benzocyclohepten-5-one hydrochloride The free base (e.e.>99% by HPLC) was dissolved in $CH_2Cl_2$, the solution was brought to acidic pH with $Et_2O$/HCl and the solvent was removed in vacuo. The resulting solid was triturated with $Et_2O$, filtered and dried, yielding the title compound. $[\alpha]^{20}_D$=+27.14 (c=0.1, MeOH). NMR (free base, 300 MHz, $CDCl_3$, δ ppm): 7.30–7.15 (m, 7H); 7.00 (d, 1H); 3.84 (s, 3H); 3.16 (ddd, 1H); 3.00–2.80 (m, 4H); 2.59 (dd, 1H); 2.50–2.49 (m, 1H); 2.30 (m, 2H); 2.25–1.90 (m, 4H); 1.81–1.72 (m, 4H); 1.55 (m, 1H).

EXAMPLE 59

(−)-1-Methoxy-7-[(4-phenylpiperidin-1-yl)methyl]-6,7,8,9-tetrahydro-5H-benzocyclohepten-5-one hydrochloride The free base (e.e.=96% by HPLC) was treated as described in the previous example, yielding the title compound. $[\alpha]^{20}_D$=−29.14 (c=0.1, MeOH). $^1H$ NMR matched that of the opposite enantiomer.

Racemic (±)-cis-1-methoxy-7-[(4-phenylpiperidin-1-yl)methyl]-6,7,8,9-tetrahydro-5H-benzocyclohepten-5-ol (compound of Example 56) was separated by preparative HPLC on chiral stationary phase (Daicel Chiracel OD, elution with 90:10:0.1 Hexane:Ethanol:Diethylamine, 12 mL/min), obtaining:

EXAMPLE 60

(+)-cis-1-methoxy-7-[(4-phenylpiperidin-1-yl)methyl]-6,7,8,9-tetrahydro-5H-benzocyclohepten-5-ol The title compound was obtained with e.e.=98% (HPLC). $[\alpha]^{20}_D$=+64.2 (c=0.1, EtOH/Hexane). $^1H$ NMR matched that of the racemate.

EXAMPLE 61

(−)-cis-1-methoxy-7-[(4-phenylpiperidin-1-yl)methyl]-6,7,8,9-tetrahydro-5H-benzocyclohepten-5-ol The title compound was obtained with e.e.=96% (HPLC). $[\alpha]^{20}_D$=−65.8 (c=0.1, EtOH/Hexane). $^1H$ NMR matched that of the racemate.

Racemic (±)-trans-1-methoxy-7-[(4-phenylpiperidin-1-yl)methyl]-6,7,8,9-tetrahydro-5H-benzocyclohepten-5-ol (compound of Example 57) was separated by preparative HPLC on chiral stationary phase (Daicel Chiracel OD, elution with 90:10:0.1 Hexane:Ethanol:Diethylamine, 12 mL/min), obtaining:

EXAMPLE 62

(+)-trans-1-methoxy-7-[(4-phenylpiperidin-1-yl)methyl]-6,7,8,9-tetrahydro-5H-benzocyclohepten-5-ol The title compound was obtained with e.e.>99% (HPLC). $[\alpha]^{20}_D$=+12.7 (c=0.5, EtOH). $^1H$ NMR matched that of the racemate.

EXAMPLE 63

(−)-trans-1-methoxy-7-[(4-phenylpiperidin-1-yl)methyl]-6,7,8,9-tetrahydro-5H-benzocyclohepten-5-ol The title compound was obtained with e.e.>97% (HPLC). $[\alpha]^{20}_D$=−12.1 (c=0.5, EtOH). $^1H$ NMR matched that of the racemate.

EXAMPLE 64

[4-(2-Methylphenyl)-N-(6,7,8,9-tetrahydro-5H-benzocyclohepten-7-yl)]piperidine The title compound was obtained according to the method described in Example 17.

IR, $^1$H nmr spectra and mass spectra were consistent with the assigned structure.

Racemic (±)-cis-1-methyl-7-[[4-(2-methylphenyl)piperidin-1-yl]methyl]-6,7,8,9-tetrahydro-5H-benzocyclohepten-5-ol (compound of Example 19) was separated by preparative HPLC on chiral stationary phase (Daicel Chiracel OD, elution with 90:10:0.1 Hexane:Ethanol:Diethylamine, 12 mL/min), obtaining:

EXAMPLE 65

(−)-cis-1-Methyl-7-[[4-(2-methylphenyl)piperidin-1-yl]methyl]-6,7,8,9-tetrahydro-5H-benzocyclohepten-5-ol The title compound was obtained with e.e.>98% (HPLC). $[\alpha]^{20}_D$=−49 (c=0.1, EtOH/Hexane). $^1$H NMR matched that of the racemate.

EXAMPLE 66

(+)-cis-1-Methyl-7-[[4-(2-methylphenyl)piperidin-1-yl]methyl]-6,7,8,9-tetrahydro-5H-benzocyclohepten-5-ol The title compound was obtained with e.e.=92% (HPLC). $[\alpha]^{20}_D$=+40 (c=0.1, EtOH/Hexane). $^1$H NMR matched that of the racemate.

Method of Nociceptin Binding Assay
Receptor Cloning and Expression

ORL-1 receptor was stably expressed in a Chinese Hamster Ovary (CHO) cell line (ACC-317) using a pCDN vector. Subclone selection was performed by growth in the absence of nucleosides. The cell line expressing high numbers of ORL-1 binding sites was selected for further characterization in radioligand binding and signal transduction assay (cAMP and GTPgS assays).

Cell Growth Conditions

CHO cells are grown in suspension, in 1017 S03 culture and maintained at 37° C. and 5% $CO_2$. The cells are routinely grown on a shaker in the presence of 0.05% (v/v) pluronic acid (F68). The maximum cell density for this CHO cell lines is $4\times10^6$ cells/ml. The cultures are passed twice a week at a 1:5 or 1:10 dilution.

Membrane Preparation by Hypotonic Lysis

All steps are performed at 4° C.
1) Harvest cells in PBS (approximately $30\times10^6$ cells/tube). Collect cells by centrifugation (1200 rpm, ca 800×g 5 min).
2) Resuspend each pellet in 10 mM dibasic phosphate buffer, pH 7.2 (buffer A)—circa 30 ml/pellet. Centrifuge 15000 rpm 10 min (Sorvall SS-34 rotor).
3) Resuspend the pellets in the same volume of buffer A, incubate on ice for 20 min.
    Centrifuge at 1200 rpm, 5 min and save the supernatants.
4) Resuspend the low speed pellets in buffer A again and repeat step 3) two more times saving the supernatants each time.
5) Pool the low speed supernatants. Spin (15000 rpm, 10 min) to collect the membranes.
6) Resuspend the pellets in buffer A containing 0.32 M sucrose and 5 mM EDTA (buffer B). Pool, spin again at high speed to concentrate the membranes and wash in this storage buffer.
7) Resuspend in buffer B the final pellet to a final concentration of 5–10 mg protein/ml (ca $10\times10^6$ cells/ml). Freeze the aliquots at −80° C.

Radioligand Binding

Radioligand binding experiments have been performed in Tris buffer pH 7.4 containing 100 ug/ml Bacitracine, 4 ug/ml Leupeptine and 2 ug/ml Chymostatine at the final volume of 1 ml, using [$^3$H]-Nociceptin (Amersham, 172 Ci/mmol) as the radioligand.

Binding experiments were carried out at 25° C. for 20 min and the reaction was terminated by filtration through Whatman GF/B filters pretreated with 0.2% PEI. Filters were washed 3 times in Tris buffer pH 7.4 at 4° C. The radioactivity present on the discs was measured by liquid scintillation counting using a 2500 Camberra Packard beta counter.

The most potent compounds in accordance with the present invention have an ORL-1 binding affinity (Ki) in the range from 1 to 1000 nM.

The stereochemistry shown for the Examples in the following Summary Table of Examples 1–66 serves to illustrate the relative stereochemistry of the compounds only.

SUMMARY TABLE OF EXAMPLES 1–66

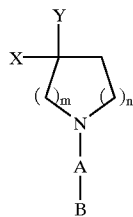

I

| Example No. | X | Y | m | n | A | B | Molecular Formula | m.p. (° C.) | $[\alpha]^{20}_D$ |
|---|---|---|---|---|---|---|---|---|---|
| 1 | Ph | H | 2 | 1 | $CH_2$ | 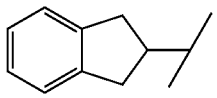 | $C_{21}H_{25}N\cdot HCl$ | >240 | — |

-continued

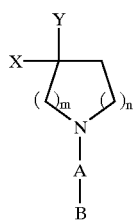

I

| Example No. | X | Y | m | n | A | B | Molecular Formula | m.p. (° C.) | $[\alpha]^{20}_D$ |
|---|---|---|---|---|---|---|---|---|---|
| 2 | Ph | H | 2 | 1 | CH$_2$ | (1-hydroxy-tetrahydronaphthalen-3-yl) | C$_{22}$H$_{27}$NO | 107–108 | — |
| 3 | Ph | H | 2 | 1 | CH$_2$ | (tetrahydronaphthalen-2-yl) | C$_{22}$H$_{27}$NHCl | 264–265 | — |
| 4 | Ph | H | 2 | 1 | CH$_2$ | (1-oxo-tetrahydronaphthalen-3-yl) | C$_{22}$H$_{25}$NOHCl | 261–262 | — |
| 5 | Ph | H | 2 | 1 | CH$_2$ | (1-oxo-tetrahydronaphthalen-3-yl, (S)) | C$_{22}$H$_{25}$NOHCl | 259–260 | −11.30 (c = 0.1, MeOH) |
| 6 | Ph | H | 2 | 1 | CH$_2$ | (1-oxo-tetrahydronaphthalen-3-yl, (R)) | C$_{22}$H$_{25}$NOHCl | 257–258 | +11.74 (c = 0.1, MeOH) |
| 7 | Ph | H | 2 | 1 | CH$_2$ | (oxo-phenanthrenyl) | C$_{26}$H$_{27}$NOHCl | — | — |
| 8 | Ph | H | 2 | 1 | CH$_2$ | (dihydronaphthalen-2-yl) | C$_{22}$H$_{25}$NHCl | 239–240 | — |

-continued
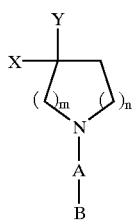
I
| Example No. | X | Y | m | n | A | B | Molecular Formula | m.p. (° C.) | $[\alpha]^{20}_D$ |
|---|---|---|---|---|---|---|---|---|---|
| 9 | Ph | H | 2 | 1 | CH$_2$ | | C$_{23}$H$_{29}$NO | 48–50 | — |
| 10 | Ph | H | 2 | 1 | CH$_2$ | | C$_{24}$H$_{31}$NO$_2$ | 46–48 | — |
| 11 | Ph | H | 2 | 1 | CH$_2$ | | C$_{24}$H$_{31}$NO$_2$ | 45–48 | — |
| 12 | Ph | H | 2 | 1 | CH$_2$ | | C$_{23}$H$_{27}$NOHCl | 220 (dec) | — |
| 13 | Ph | H | 2 | 1 | CH$_2$ | | C$_{24}$H$_{29}$NO$_2$HCl | 140–143 | — |
| 14 | Ph | H | 2 | 1 | CH$_2$ | | C$_{24}$H$_{29}$NO$_2$HCl | 185–188 | — |
| 15 | Ph | H | 2 | 1 | CH$_2$ | | C$_{24}$H$_{31}$NOHCl | 213–215 | — |

-continued
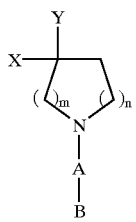
I
| Example No. | X | Y | m | n | A | B | Molecular Formula | m.p. (° C.) | $[\alpha]^{20}_D$ |
|---|---|---|---|---|---|---|---|---|---|
| 16 | Ph | H | 2 | 1 | CH₂ | | $C_{24}H_{31}NO·HCl$ | 220–222 | — |
| 17 | Ph | H | 2 | 1 | Bond | | $C_{20}H_{23}N·HCl$ | >250 | — |
| 18 | Ph | H | 2 | 1 | Bond | | $C_{22}H_{27}N·HCl$ | >250 | — |
| 19 | (2-Me)Ph | H | 2 | 1 | CH₂ | | $C_{25}H_{33}NO·HCl$ | >250 | — |
| 20 | Ph | H | 2 | 1 | CH₂ | | $C_{25}H_{33}NO$ | 52–55 | — |
| 21 | (2-OMe)Ph | H | 2 | 1 | CH₂ | | $C_{24}H_{31}NO_2$ | 72–74 | — |
| 22 | Ph | H | 2 | 1 | CH₂ | | $C_{23}H_{28}ClNO$ | — | — |

-continued
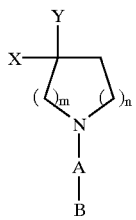
I
| Example No. | X | Y | m | n | A | B | Molecular Formula | m.p. (° C.) | $[\alpha]^{20}_D$ |
|---|---|---|---|---|---|---|---|---|---|
| 23 | Ph | H | 2 | 1 | CH$_2$ | | C$_{23}$H$_{28}$ClNO | — | — |
| 24 | (2-OH)Ph | H | 2 | 1 | CH$_2$ | | C$_{23}$H$_{29}$NO$_2$.HCl | 158–160 | — |
| 25 | (3-F)Ph | H | 2 | 1 | CH$_2$ | | C$_{23}$H$_{28}$FNO.HCl | 238–240 | — |
| 26 | (2-Me)Ph | H | 2 | 1 | CH$_2$ | | C$_{24}$H$_{31}$NO.HCl | >250 | — |
| 27 | Ph | H | 2 | 1 | CH$_2$ | | C$_{24}$H$_{31}$NO | 52–55 | — |
| 28 | (4-OBn)Ph | H | 2 | 1 | CH$_2$ | | C$_{30}$H$_{35}$NO$_2$.HCl | 225–228 | — |
| 29 | (3-Br)Ph | H | 2 | 1 | CH$_2$ | | C$_{23}$H$_{28}$BrNO.HCl | >250 | — |

-continued
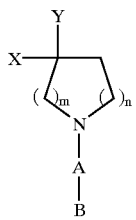
I
| Example No. | X | Y | m | n | A | B | Molecular Formula | m.p. (° C.) | $[\alpha]^{20}_D$ |
|---|---|---|---|---|---|---|---|---|---|
| 30 | Ph | H | 2 | 1 | CH$_2$ | *(1-F-benzosuberanol)* | C$_{23}$H$_{28}$FNO.HCl | 218–220 | — |
| 31 | (4-F)Ph | H | 2 | 1 | CH$_2$ | *(benzosuberanol)* | C$_{23}$H$_{28}$FNO.HCl | 227–229 | — |
| 32 | (3,5-di-OMe)Ph | H | 2 | 1 | CH$_2$ | *(benzosuberanol)* | C$_{25}$H$_{33}$NO$_3$.HCl | 223–225 | — |
| 33 | Ph | H | 2 | 1 | CH$_2$ | *(1-Ph-benzosuberanol)* | C$_{29}$H$_{33}$NO.HCl | 245–246 | — |
| 34 | (2-Cl)Ph | H | 2 | 1 | CH$_2$ | *(benzosuberanol)* | C$_{23}$H$_{28}$ClNO.HCl | 239–240 | — |
| 35 | Ph | H | 2 | 1 | CH$_2$ | *(1-Br-benzosuberanol)* | C$_{23}$H$_{28}$BrNO.HCl | 220–224 | — |

-continued

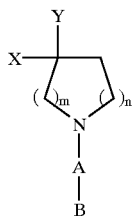

I

| Example No. | X | Y | m | n | A | B | Molecular Formula | m.p. (° C.) | $[\alpha]^{20}_D$ |
|---|---|---|---|---|---|---|---|---|---|
| 36 | Ph | H | 2 | 1 | CH$_2$ | (5-hydroxy-7-ethyl-1-benzyloxy-benzocycloheptane) | $C_{30}H_{35}NO_2 \cdot HCl$ | 198–202 | — |
| 37 | (3-F)Ph | H | 2 | 1 | CH$_2$ | (5-hydroxy-7-ethyl-1-methyl-benzocycloheptane) | $C_{24}H_{30}FNO \cdot HCl$ | 241–243 | — |
| 38 | (2-Me)Ph | H | 2 | 1 | CH$_2$ | (5-hydroxy-7-ethyl-1-methoxy-benzocycloheptane) | $C_{25}H_{33}NO_2$ | — | — |
| 39 | (2-Me)Ph | H | 2 | 1 | CH$_2$ | (5-hydroxy-7-ethyl-1-methoxy-benzocycloheptane, stereoisomer) | $C_{25}H_{33}NO_2$ | — | — |
| 40 | (3-F)Ph | H | 2 | 1 | CH$_2$ | (5-hydroxy-7-ethyl-1-methoxy-benzocycloheptane) | $C_{24}H_{30}FNO_2$ | — | — |

-continued

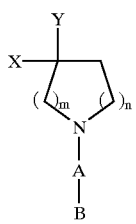

I

| Example No. | X | Y | m | n | A | B | Molecular Formula | m.p. (° C.) | $[\alpha]^{20}_D$ |
|---|---|---|---|---|---|---|---|---|---|
| 41 | (3-F)Ph | H | 2 | 1 | CH$_2$ | (structure: HO, OMe, isopropyl-substituted benzocycloheptane) | C$_{24}$H$_{30}$FNO$_2$ | — | — |
| 42 | Ph | H | 2 | 1 | CH$_2$ | (structure: HO, OH, isopropyl-substituted benzocycloheptane) | C$_{23}$H$_{29}$NO$_2$.HCl | 190–193 | — |
| 43 | Ph | H | 2 | 1 | CH$_2$ | (structure: OMe, OH, isopropyl-substituted benzocycloheptane) | C$_{24}$H$_{31}$NO$_2$ | 176–189 | — |
| 44 | Ph | H | 2 | 1 | CH$_2$ | (structure: dimethyl-substituted benzocycloheptanone with isopropyl) | C$_{25}$H$_{31}$NO.HCl | 222–225 | — |
| 45 | (2-OMe)Ph | H | 2 | 1 | CH$_2$ | (structure: benzocycloheptanone with isopropyl) | C$_{24}$H$_{29}$NO$_2$HCl | 232–234 | — |
| 46 | Ph | H | 2 | 1 | CH$_2$ | (structure: Cl-substituted benzocycloheptanone with isopropyl) | C$_{23}$H$_{26}$ClNO.HCl | 180–185 | — |
| 47 | Ph | H | 2 | 1 | CH$_2$ | (structure: Cl-substituted benzocycloheptanone with isopropyl) | C$_{23}$H$_{26}$ClNO.HCl | — | — |

-continued
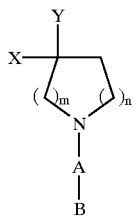
I
| Example No. | X | Y | m | n | A | B | Molecular Formula | m.p. (° C.) | $[\alpha]^{20}_D$ |
|---|---|---|---|---|---|---|---|---|---|
| 48 | (2-OH)Ph | H | 2 | 1 | CH₂ | | $C_{23}H_{27}NO_2 \cdot HCl$ | 216–218 | — |
| 49 | Ph | H | 2 | 1 | CH₂ | | $C_{24}H_{29}NO \cdot HCl$ | 205–210 | — |
| 50 | (2-Me)Ph | H | 2 | 1 | CH₂ | | $C_{24}H_{29}NO$ | 202–205 | — |
| 51 | Ph | H | 2 | 1 | CH₂ | | $C_{23}H_{27}N \cdot HCl$ | >250 | — |
| 52 | Ph | H | 2 | 1 | CH₂ | | $C_{23}H_{29}N \cdot HCl$ | >250 | — |
| 53 | (2-Me)Ph | H | 2 | 1 | CH₂ | | $C_{24}H_{31}N$ | 245 | — |
| 54 | Ph | H | 2 | 1 | CH₂ | | $C_{26}H_{33}NO \cdot HCl$ | 126–128 | — |

-continued

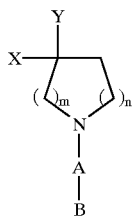

I

| Example No. | X | Y | m | n | A | B | Molecular Formula | m.p. (° C.) | $[\alpha]^{20}_D$ |
|---|---|---|---|---|---|---|---|---|---|
| 55 | Ph | H | 2 | 1 | CH$_2$ | (benzocycloheptane with HO and isopropyl) | C$_{23}$H$_{29}$NO.HCl | >250 | — |
| 56 | Ph | H | 2 | 1 | CH$_2$ | (benzocycloheptane with HO, OMe and isopropyl) | C$_{24}$H$_{31}$NO$_2$.HCl | 229–231 | — |
| 57 | Ph | H | 2 | 1 | CH$_2$ | (benzocycloheptane with HO, OMe and isopropyl) | C$_{24}$H$_{31}$NO$_2$.HCl | >250 | — |
| 58 | Ph | H | 2 | 1 | CH$_2$ | (benzocycloheptanone with OMe and isopropyl) | C$_{24}$H$_{29}$NO$_2$.HCl | — | +27.14 (c = 0.1, MeOH) |
| 59 | Ph | H | 2 | 1 | CH$_2$ | (benzocycloheptanone with OMe and isopropyl) | C$_{24}$H$_{29}$NO$_2$.HCl | — | −29.14 (c = 0.1, MeOH) |
| 60 | Ph | H | 2 | 1 | CH$_2$ | (benzocycloheptane with HO, OMe and isopropyl) | C$_{24}$H$_{31}$NO$_2$.HCl | — | +64.2 (c = 0.1, EtOH/Hexane) |

-continued
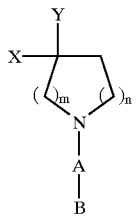
I
| Example No. | X | Y | m | n | A | B | Molecular Formula | m.p. (° C.) | $[\alpha]^{20}_D$ |
|---|---|---|---|---|---|---|---|---|---|
| 61 | Ph | H | 2 | 1 | $CH_2$ | | $C_{24}H_{31}NO_2 \cdot HCl$ | — | −65.8 (c = 0.1, EtOH/Hexane) |
| 62 | Ph | H | 2 | 1 | $CH_2$ | | $C_{24}H_{31}NO_2$ | — | +12.7 (c = 0.5, EtOH) |
| 63 | Ph | H | 2 | 1 | $CH_2$ | | $C_{24}H_{31}NO_2$ | — | −12.1 (c = 0.5, EtOH) |
| 64 | (2-Me)Ph | H | 2 | 1 | Bond | | $C_{23}H_{29}N$ | — | — |
| 65 | (2-Me)Ph | H | 2 | 1 | $CH_2$ | | $C_{25}H_{33}NO$ | — | −49 (c = 0.1, EtOH/Hexane) |
| 66 | (2-Me)Ph | H | 2 | 1 | $CH_2$ | | $C_{25}H_{33}NO$ | — | +40 (c = 0.1, EtOH/Hexane) |

What is claimed is:
1. A compound of formula I, or a salt thereof or a hydrate thereof

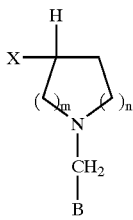

wherein,
- X is unsubstituted phenyl or phenyl substituted with $C_{1-6}$alkyl, $C_{1-6}$alkoxy, hydroxy, halo, or aryl$C_{1-6}$alkoxy;
- m is 2 and n is 1; and
- B is cycloheptyl either unsubstituted or substituted with hydroxy or oxo, and is benzo-condensed with phenyl, said phenyl group being either unsubstituted of substituted with methyl, chloro, fluoro, bromo or methoxy.

2. A compound of formula I according to claim 1 selected from:

(±)-7-[(4-Phenylpiperidin-1-yl)methyl]-6,7,8,9-tetrahydro-5H-benzocyclohepten-5-one;

(±)-7-cis-[(4-Phenylpiperidin-1-yl)methyl]-6,7,8,9-tetrahydro-5H-benzocyclobepten-5-ol;

(±)-1-Methoxy-7-[(4-phenylpiperidin-1-yl)methyl]-6,7,8,9-tetrahydro-5H-benzocyclohepten-5-ol;

(±)-3-Methoxy-7-[(4-phenylpiperidin-1-yl)methyl]-6,7,8,9-tetrahydro-5H-benzocyclohepten-5-ol;

(±)-1-Methoxy-7-[(4-phenylpiperidin-1-yl)methyl]-6,7,8,9-tetrahydro-5H-benzocyclohepten-5-one;

(±)-3-Methoxy-7-[(4-phenylpiperidin-1-yl)methyl]-6,7,8,9-tetrahydro-5H-benzocyclohepten-5-one;

(±)-cis-5-Methoxy-7-[(4-phenylpiperidin-1-yl)methyl]-6,7,8,9-tetrahydro-5H-benzocycloheptene;

(±)-trans-5-Methoxy-7-[(4-phenylpiperidin-1-yl)methyl]-6,7,8,9-tetrahydro-5H-benzocycloheptene;

(±)-cis-1-Methyl-7-[[4-(2-methylphenyl)piperidin-1-yl]methyl]-6,7,8,9-tetrahydro-5H-benzocyclohepten-5-ol;

(±)-1,3-Dimethyl-7-[(4-phenylpiperidin-1-yl)methyl]-6,7,8,9-tetrahydro-5H-benzocyclohepten-5-ol;

(±)-cis-7-[[4-(2-Methoxyphenyl)piperidin-1-yl]methyl]-6,7,8,9-tetrahydro-5H-benzocyclohepten-5-ol;

(±)-cis-3-Chloro-7-[(4-phenylpiperidin-1-yl)methyl]-6,7,8,9-tetrahydro-5H-benzocyclohepten-5-ol;

(±)-1-Chloro-7-[(4-phenylpiperidin-1-yl)methyl]-6,7,8,9-tetrahydro-5H-benzocyclohepten-5-ol;

(±)-7-[[4-(2-Hydroxyphenyl)piperidin-1-yl]methyl]-6,7,8,9-tetrahydro-5H-benzocyclohepten-5-ol;

(±)-cis-7-[[4-(3-Fluorophenyl)piperidin-1-yl]methyl]-6,7,8,9-tetrahydro-5H-benzocyclohepten-5-ol;

(±)-cis-7-[[4-(2-Methylphenyl)piperidin-1-yl]methyl]-6,7,8,9-tetrahydro-5H-benzocyclohepten-5-ol;

(±)-cis-1-Methyl-7-[(4-phenylpiperidin-1-yl)methyl]-6,7,8,9-tetrahydro-5H-benzocyclohepten-5-ol;

(±)-cis-7-[[4-(4-Benzyloxyphenyl)piperidin-1-yl]methyl]-6,7,8,9-tetrahydro-5H-benzocyclohepten-5-ol;

(±)-cis-7-[[4-(3-Bromophenyl)piperidin-1-yl]methyl]-6,7,8,9-tetrahydro-5H-benzocyclohepten-5-ol;

(±)-1-Fluoro-7-[(4-phenylpiperidin-1-yl)methyl]-6,7,8,9-tetrahydro-5H-benzocyclohepten-5-ol;

(±)-7-[[4-(4-Fluorophenyl)piperidin-1-yl]methyl]-6,7,8,9-tetrahydro-5H-benzocyclohepten-5-ol;

(±)-7-[[4-(3,5-Dimethoxyphenyl)piperidin-1-yl]methyl]-6,7,8,9-tetrahydro-5H-benzocyclohepten-5-ol;

(±)-7-[[4-(2-Chlorophenyl)piperidin-1-yl]methyl]-6,7,8,9-tetrahydro-5H-benzocyclohepten-5-ol;

(±)-cis-1-Bromo-7-[(4-phenylpiperidin-1-yl)methyl]-6,7,8,9-tetrahydro-5H-benzocyclohepten-5-ol;

(±)-cis-1-Methyl-7-[[4-(3-fluorophenyl)piperidin-1-yl]methyl]-6,7,8,9-tetrahydro-5H-benzocyclohepten-5-ol;

(±)-cis-1-Methoxy-7-[[4-(2-methylphenyl)piperidin-1-yl]methyl]-6,7,8,9-tetrahydro-5H-benzocyclohepten-5-ol;

(±)-trans-1-Methoxy-7-[[4-(2-methylphenyl)piperidin-1-yl]methyl]-6,7,8,9-tetrahydro-5H-benzocyclohepten-5-ol;

(±)-cis-1-Methoxy-7-[[4-(3-fluorophenyl)piperidin-1-yl]methyl]-6,7,8,9-tetrahydro-5H-benzocyclohepten-5-ol;

(±)-trans-1-Methoxy-7-[[4-(3-fluorophenyl)piperidin-1-yl]methyl]-6,7,8,9-tetrahydro-5H-benzocyclohepten-5-ol;

(±)-cis-1-Hydroxy-7-[(4-phenylpiperidin-1-yl)methyl]-6,7,8,9-tetrahydro-5H-benzocyclohepten-5-ol;

(±)-4-Methoxy-7-[(4-phenylpiperidin-1-yl)methyl]-6,7,8,9-tetrahydro-5H-benzocyclohepten-5-ol;

(±)-1,3-Dimethyl-7-[(4-phenylpiperidin-1-yl)methyl]-6,7,8,9-tetrahydro-5H-benzocyclohepten-5-one;

(±)-7-[[4-(2-Methoxyphenyl)piperidin-1-yl]methyl]-6,7,8,9-tetrahydro-5H-benzocyclohepten-5-one;

(±)-3-Chloro-7-[(4-pbenylpiperidin-1-yl)methyl]-6,7,8,9-tetrahydro-5H-benzocyclohepten-5-one;

(±)-1-Chloro-7-[(4-phenylpiperidin-1-yl)methyl]-6,7,8,9-tetrahydro-5H-benzocyclohepten-5-one;

(±)-7-[[4-(2-Hydroxyphenyl)piperidin-1-yl]methyl]-6,7,8,9-tetrahydro-5H-benzocyclohepten-5-one;

(±)-1-Methyl-7-[(4-phenylpiperidin-1-yl)methyl]-6,7,8,9-tetrahydro-5H-benzocyclohepten-5-one;

(±)-7-[[4-(2-Methylphenyl)piperidin-1-yl]methyl-6,7,8,9-tetrahydro-5H-benzocyclohepten-5-one;

7-[(4-Phenylpiperidin-1-yl)methyl]-6,7,8,9-tetrahydro-5H-benzocycloheptene;

7-[[4-(2-Methylphenyl)piperidin-1-yl]methyl]-6,7,8,9-tetrahydro-5H-benzocycloheptene;

(±)-trans-7-[(4-Phenylpiperidin-1-yl)methyl]-6,7,8,9-tetrahydro-5H-benzocyclohepten-5-ol;

(±)-cis-1-Methoxy-7-[(4-phenylpiperidin-1-yl)methyl]-6,7,8,9-tetrahydro-5H-benzocyclohepten-5-ol;

(±)-trans-1-Methoxy-7-[(4-phenylpiperidin-1-yl)methyl]-6,7,8,9-tetrahydro-5H-benzocyclohepten-5-ol;

(+)-1-Methoxy-7-[(4-phenylpiperidin-1-yl)methyl]-6,7,8,9-tetrahydro-5H-benzocyclohepten-5-one;

(−)-1-Methoxy-7-[(4-phenylpiperidin-1-yl)methyl]-6,7,8,9-tetrahydro-5H-benzocyclohepten-5-one;

(+)-cis-1-Methoxy-7-[(4-phenylpiperidin-1-yl)methyl]-6,7,8,9-tetrahydro-5H-benzocyclohepten-5-ol;

(−)-cis-1-Methoxy-7-[(4-phenylpiperidin-1-yl)methyl]-6,7,8,9-tetrahydro-5H-benzocyclohcpten-5-ol;

(+)-trans-1-Methoxy-7-[(4-phenylpiperidin-1-yl)methyl]-6,7,8,9-tetrahydro-5H-benzocyclohepten-5-ol;

(−)-trans-1-Methoxy-7-[(4-pbenylpiperidin-1-yl)methyl]-6,7,8,9-tetrahydro-5H-benzocyclohepten-5-ol;

[4-(2-Methylphenyl)-N-(6,7,8,9-tetrahydro-5H-benzocyclohepten-7-yl)]piperidine;

(−)-cis-1-Methyl-7-[[4-(2-methylphenyl)piperidin-1-yl]methyl]-6,7,8,9-tetrahydro-5H-benzocyclohepten-5-ol, and;

(+)-cis-1-Methyl-7-[[4-(2-methylphenyl)piperidin-1-yl]methyl]-6,7,8,9-tetrahydro-5H-benzocyclohepten-5-ol.

3. A method of antagonizing the ORL-1 receptor activity in a human or animal patient in need thereof, which method comprises administering to the human or animal patient an effective amount of a compound of formula I according to claim 1.

4. A method of treating acute pain; chronic neuropathic or inflammatory pain, including post herpetic neuralgia, neuralgia, diabetic neuropathy and post stroke pain; osteoarthritis/back pain; and painful pregnancy labour in a human or animal patient in need thereof, which method comprises administering to the human or animal patient an effective amount of a compound of formula I according to claim 1.

5. A pharmaceutical composition comprising a compound of formula I as defined in claim 1, or a pharmaceutically acceptable salt thereof or a pharmaceutically acceptable hydrate thereof, and a pharmaceutically acceptable carrier.

6. A process for the preparation of a compound of formula I, which process compnses:

a) reacting a carboxylic acid of formula V with an amine of formula III, and thereafter reducing the resulting amide of formula VI,

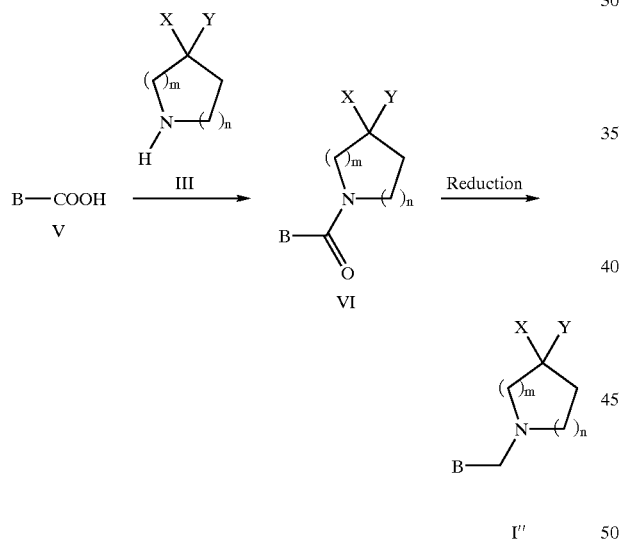

wherein B, m, n, and X are defined in accordance with formula I in claim 1, or b) reducing a carboxylic acid of formula V to an alcohol of formula VII, and reacting said alcohol with an amine of formula III,

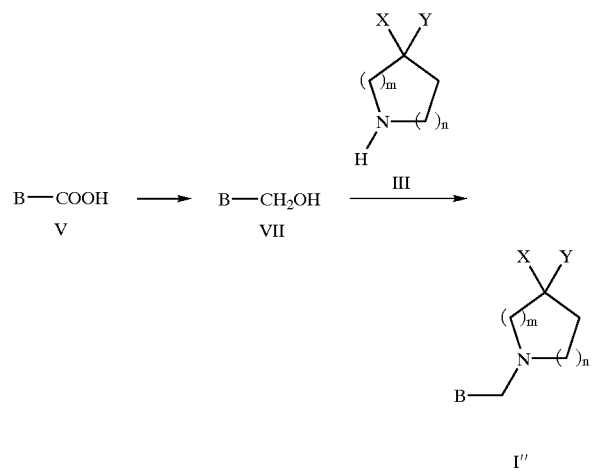

wherein B, m, n, and X are defined in accordance with formula I in claim 1, or c) oxidizing an alcohol of formula VII to an aldehyde of formula VIII, and reacting said aldehyde with an amine of formula III under reductive amination conditions,

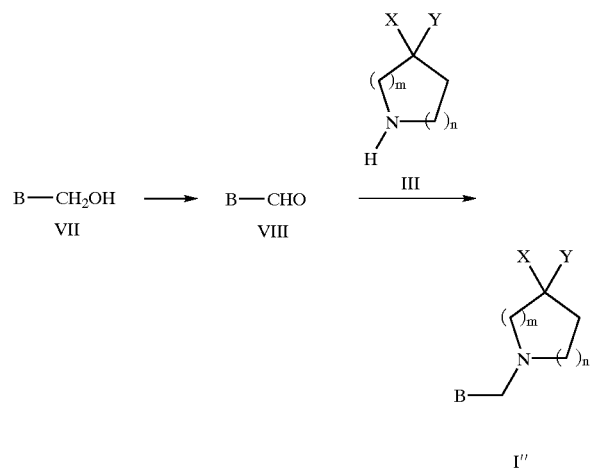

wherein B, m, n, and X are defined in accordance with formula I in claim 1.

* * * * *